United States Patent
Tsai et al.

(10) Patent No.: US 10,098,861 B1
(45) Date of Patent: Oct. 16, 2018

(54) PHARMACEUTICAL COMPOSITION COMPRISING SODIUM BENZOATE COMPOUND AND CLOZAPINE, AND USES THEREOF

(71) Applicant: SyneuRx International (Taiwan) Corp., New Taipei (TW)

(72) Inventors: Guochuan Emil Tsai, Pasadena, CA (US); Ching-Cheng Wang, New Taipei (TW)

(73) Assignee: SyneuRx International (Taiwan) Corp., New Taipei (TW)

( * ) Notice: Subject to any disclaimer, the term of this patent is extended or adjusted under 35 U.S.C. 154(b) by 0 days.

(21) Appl. No.: 15/792,088

(22) Filed: Oct. 24, 2017

(51) Int. Cl.
  *A61K 31/192* (2006.01)
  *A61K 9/20* (2006.01)
  *A61K 31/5513* (2006.01)

(52) U.S. Cl.
  CPC ............ *A61K 31/192* (2013.01); *A61K 9/205* (2013.01); *A61K 9/2013* (2013.01); *A61K 9/2059* (2013.01); *A61K 31/5513* (2013.01)

(58) Field of Classification Search
  None
  See application file for complete search history.

(56) References Cited

U.S. PATENT DOCUMENTS

| | | | |
|---|---|---|---|
| 3,498,989 A | 3/1970 | Sallay et al. | |
| 3,870,715 A | 3/1975 | Hansl | |
| 4,041,174 A | 8/1977 | Sapse | |
| 4,956,363 A | 9/1990 | Wulfert et al. | |
| 5,198,217 A | 3/1993 | Vedros | |
| 5,453,425 A | 9/1995 | Francois et al. | |
| 5,616,587 A | 4/1997 | Francois et al. | |
| 5,658,900 A | 8/1997 | Boireau et al. | |
| 6,255,089 B1 | 7/2001 | Teitler et al. | |
| 6,569,848 B1 | 5/2003 | Davis et al. | |
| 6,746,678 B1 | 6/2004 | Shapiro | |
| RE39,181 E | 7/2006 | Francois et al. | |
| 7,094,930 B2 | 8/2006 | Quallich et al. | |
| 7,166,725 B2 | 1/2007 | Fang et al. | |
| 7,811,604 B1 * | 10/2010 | Ahmed | A61K 9/0056 424/465 |
| 9,649,304 B2 | 5/2017 | Tsai | |

(Continued)

FOREIGN PATENT DOCUMENTS

DE    4340273 A1   6/1995
WO   WO 2002/066672 A2   8/2002

(Continued)

OTHER PUBLICATIONS

Lin et al. ("PM405. Sodium Benzoate Add-on Treatment for Refractory Schizophrenia: A Randomized, Double-Blind, Placebo-Controlled Trial," Int. J. Neuropsychopharmacol. Jun. 2016; 19 (Suppl 1): 47.*

(Continued)

*Primary Examiner* — Aradhana Sasan
(74) *Attorney, Agent, or Firm* — Wolf, Greenfield & Sacks, P.C.

(57) ABSTRACT

The present invention relates to a pharmaceutical composition comprising a sodium benzoate compound and clozapine; and a method for preventing, treating and/or reducing the risk of a neuropsychiatric disorder by administering such pharmaceutical composition.

6 Claims, 17 Drawing Sheets

(56) References Cited

U.S. PATENT DOCUMENTS

| | | | |
|---|---|---|---|
| 9,675,604 B2 | 6/2017 | Tsai | |
| 2001/0044446 A1 | 11/2001 | Phillips et al. | |
| 2003/0185754 A1 | 10/2003 | Cohen et al. | |
| 2004/0087658 A1 | 5/2004 | Moebius | |
| 2004/0138197 A1 | 7/2004 | Maw et al. | |
| 2004/0138298 A1 | 7/2004 | Mermelstein et al. | |
| 2005/0272721 A1 | 12/2005 | Keltjens | |
| 2006/0204486 A1* | 9/2006 | Pyke | A61K 9/2009 424/94.2 |
| 2008/0045512 A1 | 2/2008 | Duplantier et al. | |
| 2008/0070984 A1 | 3/2008 | Tran | |
| 2010/0189818 A1* | 7/2010 | Tsai | A61K 31/11 424/722 |
| 2011/0045065 A1* | 2/2011 | Vyas | C07D 213/30 424/452 |
| 2016/0008476 A1 | 1/2016 | Embrechts et al. | |
| 2017/0181989 A1* | 6/2017 | Tsai | A61K 31/192 |
| 2017/0189358 A1 | 7/2017 | Tsai | |
| 2018/0036267 A1* | 2/2018 | Tsai | A61K 31/192 |
| 2018/0111891 A1 | 4/2018 | Tsai et al. | |

FOREIGN PATENT DOCUMENTS

| | | |
|---|---|---|
| WO | WO 2005/000205 A2 | 1/2005 |
| WO | WO 2005/117911 A2 | 12/2005 |
| WO | WO 2006/129160 A2 | 12/2006 |
| WO | WO 2007/093829 A1 | 8/2007 |
| WO | WO 2010/085452 A1 | 7/2010 |

OTHER PUBLICATIONS

Lin et al. ("Sodium Benzoate, a D-Amino Acid Oxidase Inhibitor, Added to Clozapine for the Treatment of Schizophrenia: A Randomized, Double-Blind, Placebo-Controlled Trial," Biological Psychiatry, Available online Dec. 26, 2017, pp. 1-11.*

Butterhof et al., Microphase Separation with Small Amphiphilic Molecules: Crystal Structure of Preservatives Sodium Benzoate (E 211) and Potassium Benzoate (E 212). Z. Anorg. Allg. Chem. 2013;639(15):2816-21.

Howard et al., A Process Analytical Technology Based Investigation of the Polymorphic Transformations during the Antisolvent Crystallization of Sodium Benzoate from IPA/Water Mixture. Crystal Growth & Design. 2009;9(9):3964-75.

Inoue et al., The relationship between crystal morphology and XRD peak intensity on $CaSO_4 \cdot 2H_2O$. J Crystal Growth. Oct. 1, 2013;380:169-175.

Millan et al., Overview of drug classes proposed for the treatment of cognitive impairments in psychiatric disorders. table 2, Feb. 2012. 1-7, www.nature.com/nrd/journal/v11/n2/fig.sub.—tab/nrd3628.sub.T2.html.

Smith et al., The Therapeutic Potential of D-Amino Acid Oxidase (DAAO) Inhibitors. 2010;4:3-9. The Open Medicinal Chemistry Journal.

Stern et al., Ageing and detoxication; studies in hippuric acid synthesis during psychoses of the involutional and old age group. Am J Psychiatry. Nov. 1945;102:325-9.

* cited by examiner

PHARMACEUTICAL COMPOSITION COMPRISING SODIUM BENZOATE COMPOUND AND CLOZAPINE, AND USES THEREOF

BACKGROUND OF THE INVENTION

The central nervous system (CNS) includes the brain and spinal cord. The CNS is vulnerable to various disorders, which may be caused by various factors, including genetic, trauma, infections, degeneration, structural defects and/or damages, tumors, blood flow disruption, and autoimmune disorders. Symptoms of a CNS disorder would depend on the area of the nervous system that is involved and the cause of the disorder.

The development of effective therapies for CNS disorders has lagged behind other therapeutic areas due to the complexity of such disorders and the lack of efficient technology for delivering therapeutic agents through the blood-brain barrier. As such, it is of great interest to develop new treatment approaches for CNS disorders.

SUMMARY OF THE INVENTION

Provided herein are pharmaceutical compositions comprising a sodium benzoate compound and clozapine; and a method for treating and/or reducing the risk of a neuropsychiatric disorder by administering such pharmaceutical composition.

In one aspect, the present disclosure provides a pharmaceutical composition comprising 50 to 1000 mg of a sodium benzoate compound and 25 to 300 mg of clozapine in a solid dosage form, e.g., tablet, dragee, capsule, pill, powder, or granule. In some embodiments, the solid dosage form may further comprise a film coating.

The aforementioned sodium benzoate compound can be in amorphous form, in polymorphic forms, or both. In some embodiments, the sodium benzoate compound comprises a polymorphic form of sodium benzoate, which may have an X-ray powder diffraction pattern comprising characteristic peaks at a reflection angle 2θ of about 5.9, 30.2 and 31.2 degrees. In one example, the polymorphic form of sodium benzoate can be characterized by an X-ray powder diffraction pattern further comprising characteristic peaks at a reflection angle 2θ of about 4.3, 7.1, 8.6, 10.1, 10.7, 12.9, 13.8, 14.4, 17.2, 17.7, 18.5, 21.5, 22.0, 22.6, 23.7, 25.1, 25.9, 26.2, 26.9, 27.9, 28.2, 28.8, 29.1, 29.7, 33.2, 34.9, 35.8, 36.1, 39.3 degrees.

Any of the pharmaceutical compositions described herein may further comprise a pharmaceutically acceptable excipient, which may be boric acid, sodium alginate, sodium citrate, sodium hyaluronate, chitosan, magnesium stearate, sodium stearyl fumarate, colloidal silicon dioxide, talc, sodium starch glycolate, croscarmellose, crospovidone, tannic acid, or a combination thereof. In some embodiments, the pharmaceutical composition may comprise 50 to 1000 mg of sodium benzoate, 25-300 mg of clozapine, 50-500 mg of sodium alginate, 50-400 mg of sodium citrate, 5-100 mg of magnesium stearate, and 80-200 mg of sodium starch glycolate.

In another aspect, the present disclosure provides a method for treating and/or reducing the risk for a neuropsychiatric disorder, which comprises administering to a subject in need of the treatment an effective amount of any of the pharmaceutical compositions described herein. Target neuropsychiatric disorders include, but are not limited to, schizophrenia, psychotic disorders, Alzheimer's disease, dementia, frontotemporal dementia, mild cognitive impairment, benign forgetfulness, closed head injury, autistic spectrum disorder, Asperger's disorder, attention deficit hyperactivity disorders, obsessive compulsive disorder, tic disorders, childhood learning disorders, premenstrual syndrome, depression, suicidal ideation and/or behaviors, bipolar disorder, anxiety disorders, post-traumatic stress disorder, chronic pain, eating disorders, addiction disorders, personality disorders, Parkinson's disorder, Huntington's disorder, multiple sclerosis, or amyotrophic lateral sclerosis.

In some embodiments, the subject can be a human patient having, suspected of having, or at risk for the neuropsychiatric disorder. The pharmaceutical composition may be administered to the subject by a systemic route, e.g., enteral administration or parenteral administration. In some instances, the subject is administered the pharmaceutical composition at a frequency of four times a day to one time two months. Alternatively or in addition, the subject is treated concurrently with, prior to, or subsequent to one or more additional therapeutic agents for treating and/or reducing the risk for the neuropsychiatric disorder.

Also within the present disclosure are any of the pharmaceutical compositions described herein for use in treating a neuropsychiatric disorder, and uses of such for manufacturing a medicament for treating the target disease.

The details of one or more embodiments of the disclosure are set forth herein. Other features, objects, and advantages of the disclosure will be apparent from the Detailed Description, the Examples, and the Claims.

DEFINITIONS

Definitions of specific functional groups and chemical terms are described in more detail below. The chemical elements are identified in accordance with the Periodic Table of the Elements, CAS version, *Handbook of Chemistry and Physics*, 75th Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3rd Edition, Cambridge University Press, Cambridge, 1987. The disclosure is not intended to be limited in any manner by the exemplary listing of substituents described herein.

The term "sodium benzoate compound" refers to a compound of the formula

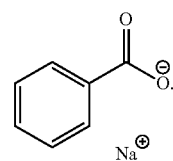

The term "crystalline" or "crystalline form" refers to a solid form substantially exhibiting three-dimensional order. In certain embodiments, a crystalline form of a solid is a solid form that is substantially not amorphous. In certain embodiments, the X-ray powder diffraction (XRPD) pattern of a crystalline form includes one or more sharply defined peaks.

The term "clozapine" refers to the compound with the IAPUC name of 3-chloro-6-(4-methylpiperazin-1-yl)-5H-benzo[b][1,4]benzodiazepine.

The term "amorphous" or "amorphous form" refers to a form of a solid ("solid form"), the form substantially lacking three-dimensional order. In certain embodiments, an amorphous form of a solid is a solid form that is substantially not crystalline. In certain embodiments, the X-ray powder diffraction (XRPD) pattern of an amorphous form includes a wide scattering band with a peak at 2θ of, e.g., between 20 and 70°, inclusive, using CuKα radiation. In certain embodiments, the XRPD pattern of an amorphous form further includes one or more peaks attributed to crystalline structures. In certain embodiments, the maximum intensity of any one of the one or more peaks attributed to crystalline structures observed at a 2θ of between 20 and 70°, inclusive, is not more than 300-fold, not more than 100-fold, not more than 30-fold, not more than 10-fold, or not more than 3-fold of the maximum intensity of the wide scattering band. In certain embodiments, the XRPD pattern of an amorphous form includes no peaks attributed to crystalline structures.

The term "polymorph" or "polymorphic form" refers to a crystalline form of a compound (or a salt, hydrate, or solvate thereof). All polymorphic forms have the same elemental composition. Different crystalline forms usually have different X-ray diffraction patterns, infrared spectra, melting points, density, hardness, crystal shape, optical and electrical properties, stability, and solubility. Recrystallization solvent, rate of crystallization, storage temperature, and other factors may cause one crystal form to dominate. Various polymorphic forms of a compound can be prepared by crystallization under different conditions.

The term "commercially available sodium benzoate" refers to sodium benzoate available from commercial source, which may be in amorphous form, may comprise a known single polymorphic form, or may comprise a mixture of amorphous and/or one or more polymorphic forms.

The terms "crystalline sodium benzoate" or "polymorphic form of sodium benzoate" refer to a purified polymorphic form of sodium benzoate with a specific X-ray powder diffraction (XRPD) pattern comprising characteristic peaks at a reflection angle 2θ of about 5.9, 30.2 and 31.2 degrees. In some embodiments, the crystalline sodium benzoate of the invention is a purified polymorphic form of sodium benzoate having an XRPD pattern with peaks (°) of: 3.6, 5.9, 7.2, 7.5, 14.9, 15.9, 16.6, 17.6, 18.8, 20.4, 22.9, 23.7, 25.1, 25.8, 26.6, 28.1, 29.1, 29.4, 29.7, 30.2, 31.2, 31.5, 32.9, 34.2, 35.7. In some embodiments, the crystalline sodium benzoate of the invention is a purified polymorphic form of sodium benzoate having an XRPD pattern with peaks (°) of: 3.7, 5.9, 6.8, 7.5, 11.3, 11.6, 17.6, 22.7, 23.5, 26.2, 27.6, 28.3, 29.3; 30.2, 31.2, 32.2, 32.9, 34.0, 35.7. In some embodiments, the crystalline sodium benzoate of the invention is a purified polymorphic form of sodium benzoate having an XRPD pattern with peaks (°) of: 3.7, 5.9, 6.3, 6.8, 7.5, 11.7, 17.7, 23.6, 24.5, 26.5, 27.0, 27.7, 28.4, 29.0, 30.2; 31.0, 31.2, 32.3, 34.2, 35.9. In some embodiments, the crystalline sodium benzoate of the invention is a purified polymorphic form of sodium benzoate having an XRPD pattern with peaks (°) of: 4.3, 5.9, 7.1, 8.6, 10.1, 10.7, 12.9, 13.8, 14.4, 17.2, 17.7, 18.5, 21.5, 22.0, 22.6, 23.7, 25.1, 25.9, 26.2, 26.9, 27.9, 28.2, 28.8, 29.1, 29.7, 30.2, 31.2, 33.2, 34.9, 35.8, 36.1, 39.3.

When a polymorphic form, pharmaceutical composition, method, use, or kit is referred to as "selectively," "specifically," or "competitively" binding a first protein, the polymorphic form binds the first protein with a higher binding affinity (e.g., not less than about 2-fold, not less than about 5-fold, not less than about 10-fold, not less than about 30-fold, not less than about 100-fold, not less than about 1,000-fold, or not less than about 10,000-fold) than binding a second protein that is different from the first protein. When a polymorphic form is referred to as "selectively," "specifically," or "competitively" modulating (e.g., increasing or inhibiting) the activity of a first protein, the polymorphic form modulates the activity of the first protein to a greater extent (e.g., not less than about 2-fold, not less than about 5-fold, not less than about 10-fold, not less than about 30-fold, not less than about 100-fold, not less than about 1,000-fold, or not less than about 10,000-fold) than the activity of at least one protein that is different from the first protein.

The terms "composition" and "formulation" are used interchangeably.

A "subject" to which administration is contemplated refers to a human (i.e., male or female of any age group, e.g., pediatric subject (e.g., infant, child, or adolescent) or adult subject (e.g., young adult, middle-aged adult, or senior adult)) or non-human animal. A "patient" refers to a human subject in need of treatment of a disease. For example, the subject can be a human patient having, suspected of having, or at risk for a target disease as described herein.

The terms "administer," "administering," or "administration" refers to implanting, absorbing, ingesting, injecting, inhaling, or otherwise introducing the pharmaceutical composition, in or on a subject.

The terms "treatment," "treat," and "treating" refer to reversing, alleviating, delaying the onset of, or inhibiting the progress of a disease described herein. In some embodiments, treatment may be administered after one or more signs or symptoms of the disease have developed or have been observed. In other embodiments, treatment may be administered in the absence of signs or symptoms of the disease. For example, treatment may be administered to a susceptible subject prior to the onset of symptoms (e.g., in light of a history of symptoms and/or in light of exposure to a pathogen) to delay or prevent disease occurrence. Treatment may also be continued after symptoms have resolved, for example, to delay or prevent recurrence.

The terms "inhibition", "inhibiting", "inhibit," or "inhibitor" refer to the ability of a polymorphic form to reduce, slow, halt or prevent activity of a particular biological process in a cell relative to vehicle.

The terms "condition," "disease," and "disorder" are used interchangeably.

An "effective amount" of any of the active ingredients described herein (e.g. any of the sodium benzoate compounds and/or clozapine) refers to an amount sufficient to elicit the desired biological response, i.e., treating the condition. As will be appreciated by those of ordinary skill in this art, the effective amount of any of the active ingredients described herein may vary depending on such factors as the desired biological endpoint, the pharmacokinetics of the polymorphic form, the condition being treated, the mode of administration, and the age and health of the subject. In certain embodiments, an effective amount is a therapeutically effective amount. In certain embodiments, an effective amount is a prophylactically effective amount. In certain embodiments, an effective amount is the amount of any of the active ingredients described herein in a single dose. In certain embodiments, an effective amount is the combined amounts of the active ingredients described herein in multiple doses.

A "therapeutically effective amount" of any of the active ingredients described herein is an amount sufficient to provide a therapeutic benefit in the treatment of a condition or to delay or minimize one or more symptoms associated with the condition. A therapeutically effective amount of any of the active ingredients described herein means an amount of therapeutic agent, alone or in combination with other therapies, which provides a therapeutic benefit in the treatment of the condition. The term "therapeutically effective amount" can encompass an amount that improves overall therapy, reduces or avoids symptoms, signs, or causes of the condition, and/or enhances the therapeutic efficacy of another therapeutic agent.

A "prophylactically effective amount" of any of the active ingredients described herein is an amount sufficient to prevent a condition, or one or more symptoms associated with the condition or prevent its recurrence. A prophylactically effective amount of any of the active ingredients means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

The terms "about" or "approximately," which are used interchangeably herein, means within an acceptable error range for the particular value as determined by one of ordinary skill in the art, which will depend in part on how the value is measured or determined, i.e., the limitations of the measurement system. For example, "about" or "approximately" can mean a range of less than ±10%, preferably less than ±5%, more preferably less than ±1%, more preferably less than ±0.5% of a given value. Where particular values are described in the application and claims, unless otherwise stated, the term "about" is implicit and in this context means within an acceptable error range for the particular value.

The term "neuropsychiatric disorder," including either neurological diseases or psychiatric disorders or central nervous system disorders (CNS disorders), refers to a disorder that involves either psychiatric symptoms or syndromes caused by organic central nervous system disorders. The main characteristics of neuropsychiatric symptoms include occurrence of the various psychiatric symptoms, cognitive impairment, neurological symptoms or the possibility of early cerebral development symptoms.

The term "neurological disease" refers to any disease of the nervous system, including diseases that involve the central nervous system (brain, brainstem, spinal cord, and cerebellum), the peripheral nervous system (including cranial nerves), and the autonomic nervous system (parts of which are located in both central and peripheral nervous system). Neurodegenerative diseases refer to a type of neurological disease marked by the loss of nerve cells, including, but not limited to, Alzheimer's disease, Parkinson's disease, frontotemporal dementia, multiple sclerosis, amyotrophic lateral sclerosis, tauopathies (including frontotemporal dementia), multiple system atrophy, and Huntington's disease. Examples of neurological diseases include, but are not limited to, headache, stupor and coma, dementia, seizure, sleep disorders, trauma, infections, neoplasms, neuro-ophthalmopathy, movement disorders, demyelinating diseases, spinal cord disorders, and disorders of peripheral nerves, muscle and neuromuscular junctions. Addiction and mental illness, include, but are not limited to, bipolar disorder, depression and schizophrenia, are also included in the definition of CNS diseases. Further examples of neurological diseases include acquired epileptiform aphasia; acute disseminated encephalomyelitis; adrenoleukodystrophy; agenesis of the corpus callosum; agnosia; Aicardi syndrome; Alexander disease; Alpers' disease; alternating hemiplegia; Alzheimer's disease; amyotrophic lateral sclerosis; anencephaly; Angelman syndrome; angiomatosis; anoxia; aphasia; apraxia; arachnoid cysts; arachnoiditis; Arnold-Chiari malformation; arteriovenous malformation; Asperger syndrome; ataxia telangiectasia; attention deficit hyperactivity disorder; autism; autonomic dysfunction; back pain; Batten disease; Behcet's disease; Bell's palsy; benign essential blepharospasm; benign focal amyotrophy; benign intracranial hypertension; Binswanger's disease; blepharospasm; Bloch Sulzberger syndrome; brachial plexus injury; brain abscess; brain injury; brain tumors (including glioblastoma multiforme); spinal cord tumor; Brown-Sequard syndrome; Canavan disease; carpal tunnel syndrome (CTS); causalgia; central pain syndrome; central pontine myelinolysis; cephalic disorder; cerebral aneurysm; cerebral arteriosclerosis; cerebral atrophy; cerebral gigantism; cerebral palsy; Charcot-Marie-Tooth disease; chemotherapy-induced neuropathy and neuropathic pain; Chiari malformation; chorea; chronic inflammatory demyelinating polyneuropathy (CIDP); chronic pain; chronic regional pain syndrome; Coffin Lowry syndrome; coma, including persistent vegetative state; congenital facial diplegia; corticobasal degeneration; cranial arteritis; craniosynostosis; Creutzfeldt-Jakob disease; cumulative trauma disorders; Cushing's syndrome; cytomegalic inclusion body disease (CIBD); cytomegalovirus infection; dancing eyes-dancing feet syndrome; Dandy-Walker syndrome; Dawson disease; De Morsier's syndrome; Dejerine-Klumpke palsy; dementia; dermatomyositis; diabetic neuropathy; diffuse sclerosis; dysautonomia; dysgraphia; dyslexia; dystonias; early infantile epileptic encephalopathy; empty sella syndrome; encephalitis; encephaloceles; encephalotrigeminal angiomatosis; epilepsy; Erb's palsy; essential tremor; Fabry's disease; Fahr's syndrome; fainting; familial spastic paralysis; febrile seizures; Fisher syndrome; Friedreich's ataxia; frontotemporal dementia and other "tauopathies"; Gaucher's disease; Gerstmann's syndrome; giant cell arteritis; giant cell inclusion disease; globoid cell leukodystrophy; Guillain-Barre syndrome; HTLV-1 associated myelopathy; Hallervorden-Spatz disease; head injury; headache; hemifacial spasm; hereditary spastic paraplegia; heredopathia atactica polyneuritiformis; herpes zoster oticus; herpes zoster; Hirayama syndrome; HIV-associated dementia and neuropathy (see also neurological manifestations of AIDS); holoprosencephaly; Huntington's disease and other polyglutamine repeat diseases; hydranencephaly; hydrocephalus; hypercortisolism; hypoxia; immune-mediated encephalomyelitis; inclusion body myositis; incontinentia pigmenti; infantile phytanic acid storage disease; Infantile Refsum disease; infantile spasms; inflammatory myopathy; intracranial cyst; intracranial hypertension; Joubert syndrome; Kearns-Sayre syndrome; Kennedy disease; Kinsbourne syndrome; Klippel Feil syndrome; Krabbe disease; Kugelberg-Welander disease; kuru; Lafora disease; Lambert-Eaton myasthenic syndrome; Landau-Kleffner syndrome; lateral medullary (Wallenberg) syndrome; learning disabilities; Leigh's disease; Lennox-Gastaut syndrome; Lesch-Nyhan syndrome; leukodystrophy; Lewy body dementia; lissencephaly; locked-in syndrome; Lou Gehrig's disease (aka motor neuron disease or amyotrophic lateral sclerosis); lumbar disc disease; lyme disease-neurological sequelae; Machado-Joseph disease;

macrencephaly; megalencephaly; Melkersson-Rosenthal syndrome; Menieres disease; meningitis; Menkes disease; metachromatic leukodystrophy; microcephaly; migraine; Miller Fisher syndrome; mini-strokes; mitochondrial myopathies; Mobius syndrome; monomelic amyotrophy; motor neurone disease; moyamoya disease; mucopolysaccharidoses; multi-infarct dementia; multifocal motor neuropathy; multiple sclerosis and other demyelinating disorders; multiple system atrophy with postural hypotension; muscular dystrophy; myasthenia gravis; myelinoclastic diffuse sclerosis; myoclonic encephalopathy of infants; myoclonus; myopathy; myotonia congenital; narcolepsy; neurofibromatosis; neuroleptic malignant syndrome; neurological manifestations of AIDS; neurological sequelae of lupus; neuromyotonia; neuronal ceroid lipofuscinosis; neuronal migration disorders; Niemann-Pick disease; O'Sullivan-McLeod syndrome; occipital neuralgia; occult spinal dysraphism sequence; Ohtahara syndrome; olivopontocerebellar atrophy; opsoclonus myoclonus; optic neuritis; orthostatic hypotension; overuse syndrome; paresthesia; Parkinson's disease; paramyotonia congenita; paraneoplastic diseases; paroxysmal attacks; Parry Romberg syndrome; Pelizaeus-Merzbacher disease; periodic paralyses; peripheral neuropathy; painful neuropathy and neuropathic pain; persistent vegetative state; pervasive developmental disorders; photic sneeze reflex; phytanic acid storage disease; Pick's disease; pinched nerve; pituitary tumors; polymyositis; porencephaly; Post-Polio syndrome; postherpetic neuralgia (PHN); postinfectious encephalomyelitis; postural hypotension; Prader-Willi syndrome; primary lateral sclerosis; prion diseases; progressive; hemifacial atrophy; progressive multifocal leukoencephalopathy; progressive sclerosing poliodystrophy; progressive supranuclear palsy; pseudotumor cerebri; Ramsay-Hunt syndrome (Type I and Type II); Rasmussen's Encephalitis; reflex sympathetic dystrophy syndrome; Refsum disease; repetitive motion disorders; repetitive stress injuries; restless legs syndrome; retrovirus-associated myelopathy; Rett syndrome; Reye's syndrome; Saint Vitus Dance; Sandhoff disease; Schilder's disease; schizencephaly; septo-optic dysplasia; shaken baby syndrome; shingles; Shy-Drager syndrome; Sjogren's syndrome; sleep apnea; Soto's syndrome; spasticity; spina bifida; spinal cord injury; spinal cord tumors; spinal muscular atrophy; stiff-person syndrome; stroke; Sturge-Weber syndrome; subacute sclerosing panencephalitis; subarachnoid hemorrhage; subcortical arteriosclerotic encephalopathy; sydenham chorea; syncope; syringomyelia; tardive dyskinesia; Tay-Sachs disease; temporal arteritis; tethered spinal cord syndrome; Thomsen disease; thoracic outlet syndrome; tic douloureux; Todd's paralysis; Tourette syndrome; transient ischemic attack; transmissible spongiform encephalopathies; transverse myelitis; traumatic brain injury; tremor; trigeminal neuralgia; tropical spastic paraparesis; tuberous sclerosis; vascular dementia (multi-infarct dementia); vasculitis including temporal arteritis; Von Hippel-Lindau Disease (VHL); Wallenberg's syndrome; Werdnig-Hoffman disease; West syndrome; whiplash; Williams syndrome; Wilson's disease; and Zellweger syndrome.

The term "psychiatric disorder" refers to mental disorders and includes diseases and disorders listed in the Diagnostic and Statistical Manual of Mental Disorders—Fourth Edition and Fifth Edition (DSM-IV, DSM-V), published by the American Psychiatric Association, Washington D. C. (1994, 2013). Psychiatric disorders include, but are not limited to, anxiety disorders (e.g., acute stress disorder, agoraphobia, generalized anxiety disorder, obsessive-compulsive disorder, panic disorder, posttraumatic stress disorder, separation anxiety disorder, social phobia, and specific phobia), childhood disorders, (e.g., attention-deficit/hyperactivity disorder, conduct disorder, and oppositional defiant disorder), eating disorders (e.g., anorexia nervosa and bulimia nervosa), mood disorders (e.g., depression, bipolar disorder I and II, cyclothymic disorder, dysthymic disorder, and major depressive disorder), personality disorders (e.g., antisocial personality disorder, avoidant personality disorder, borderline personality disorder, dependent personality disorder, histrionic personality disorder, narcissistic personality disorder, obsessive-compulsive personality disorder, paranoid personality disorder, schizoid personality disorder, and schizotypal personality disorder), psychotic disorders (e.g., brief psychotic disorder, delusional disorder, schizoaffective disorder, schizophreniform disorder, schizophrenia, and shared psychotic disorder), substance-related disorders (e.g., alcohol dependence or abuse, amphetamine dependence or abuse, cannabis dependence or abuse, cocaine dependence or abuse, hallucinogen dependence or abuse, inhalant dependence or abuse, nicotine dependence or abuse, opioid dependence or abuse, phencyclidine dependence or abuse, and sedative dependence or abuse), adjustment disorders, autism, Asperger's disorder, delirium, dementia, multi-infarct dementia, learning and memory disorders (e.g., amnesia and age-related memory loss), tic disorder and Tourette's disorder.

As used herein, the term "personality disorders" refers to mental disorders characterized by enduring maladaptive patterns of behavior, cognition, and inner experience, exhibited across many contexts and deviating markedly from those accepted by the individual's culture. These patterns develop early, are inflexible, and are associated with significant distress or disability. For example, the personality disorders can include, but not limited to, paranoid, schizoid, schizotypal, antisocial, borderline, histrionic, narcissistic, avoidant, dependent, and obsessive-compulsive personality disorder.

DETAILED DESCRIPTION

The present disclosure provides a pharmaceutical composition comprises an effective amount of a sodium benzoate compound and an effective amount of clozapine. The crystalline sodium benzoate of the invention (i.e. the polymorphic form of sodium benzoate) is more stable than the amorphous and the other known polymorphic forms of sodium benzoate or their combinations. Additionally, the excipients comprised in the pharmaceutical composition described herein improve the stability of the combination of the sodium benzoate compound and clozapine. The pharmaceutical composition described herein is useful in preventing, treating and/or reducing the risk for various diseases and disorders, including neuropsychiatric disorders, in a subject. Thus, also provided herein is a method for preventing, treating and/or reducing the risk for any of the target diseases described herein by administering the pharmaceutical composition described herein.

Pharmaceutical Composition

The present disclosure provides a pharmaceutical composition comprising an effective amount of a sodium benzoate compound and an effective amount of clozapine. In certain embodiments, the pharmaceutical composition comprises 50 to 1000 mg of sodium benzoate compound (e.g., 100 to 800 mg, 200 to 600 mg, or 300 to 500 mg) and 25 to 300 mg of clozapine (e.g., 50 to 250 mg, 100 to 200 mg, or 150-300 mg). In certain embodiments, the pharmaceutical composition comprises 500 mg of sodium benzoate compound and 200 to 300 mg of clozapine.

In some embodiments, the sodium benzoate compound (e.g., sodium benzoate) can be in amorphous form, or in one or more polymorphic forms. In some examples, the sodium benzoate can be mixture of amorphous form and one or more polymorphic forms. In one example, the sodium benzoate compound can be a commercially available sodium benzoate, which may include amorphous and a variety of polymorphic forms of sodium benzoate (e.g. purchased from Merck, Formosa, Sigma Aldrich, and the like), and the purified polymorphic form of sodium benzoate of the invention. In some embodiments, the sodium benzoate compound comprises a polymorphic form of sodium benzoate, which may have an X-ray powder diffraction pattern at a reflection angle 2θ comprising characteristic peaks at 5.9, 30.2 and 31.2 degrees.

Figure 1:
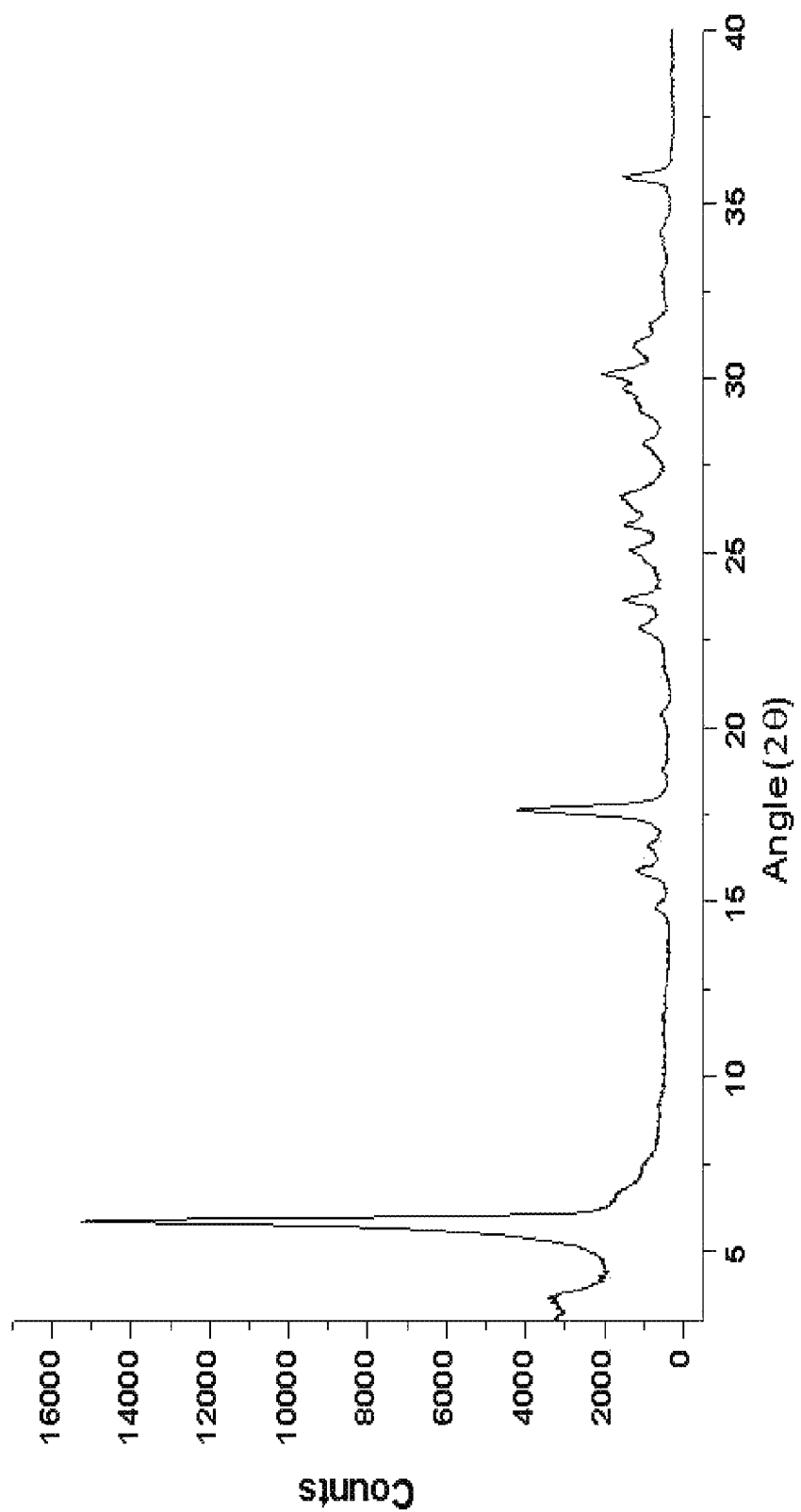
FIG. 1 shows the X-ray powder diffraction (XRPD) of polymorphic form #1 of sodium benzoate from Example 1, with peaks (°) of: 3.6, 5.9, 7.2, 7.5, 14.9, 15.9, 16.6, 17.6, 18.8, 20.4, 22.9, 23.7, 25.1, 25.8, 26.6, 28.1, 29.1, 29.4, 29.7, 30.2, 31.2, 31.5, 32.9, 34.2, 35.7.
Figure 2:
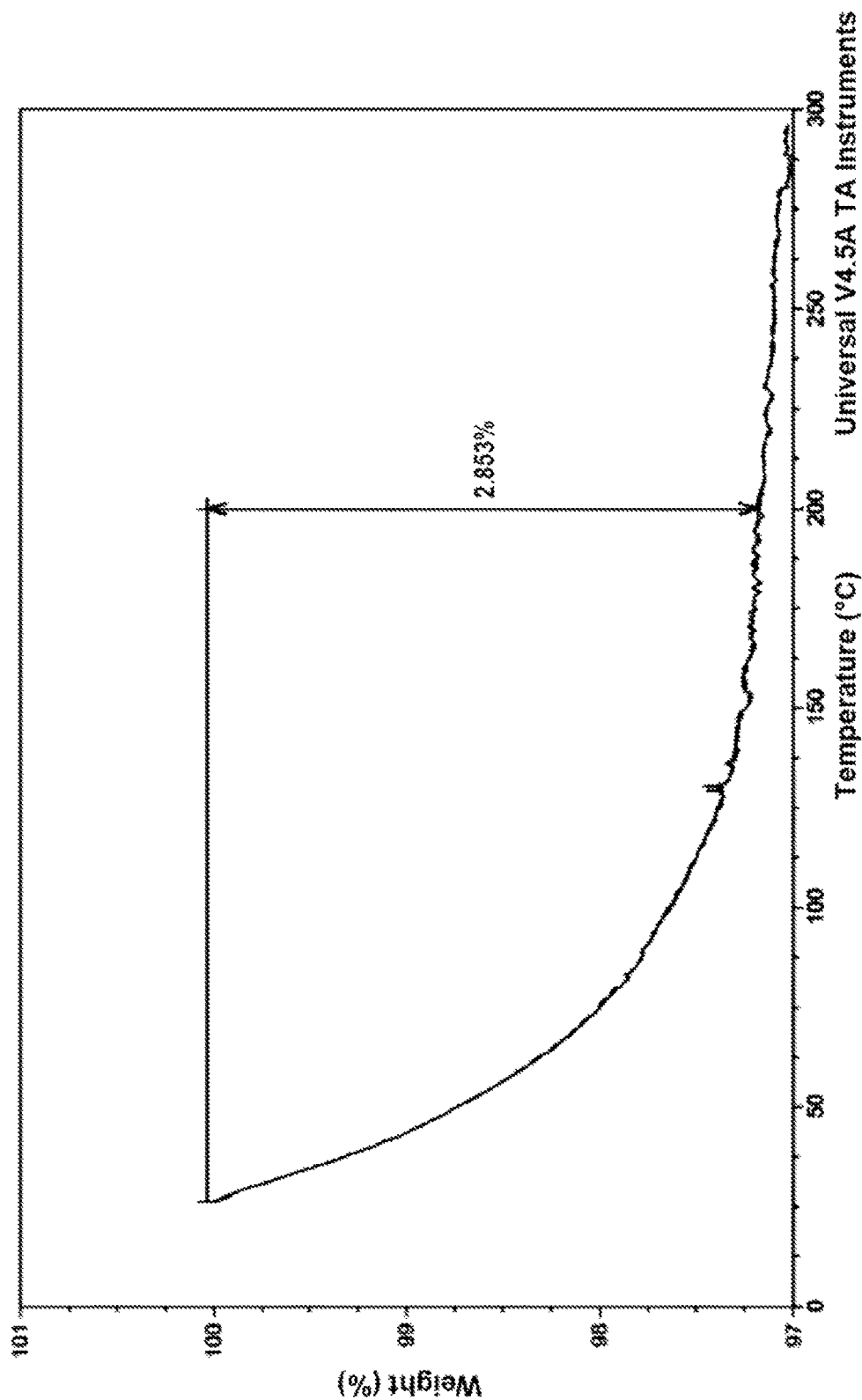
FIG. 2 shows the Thermogravimetric Analysis (TGA) of polymorphic form #1 of sodium benzoate from Example 1.
Figure 3:
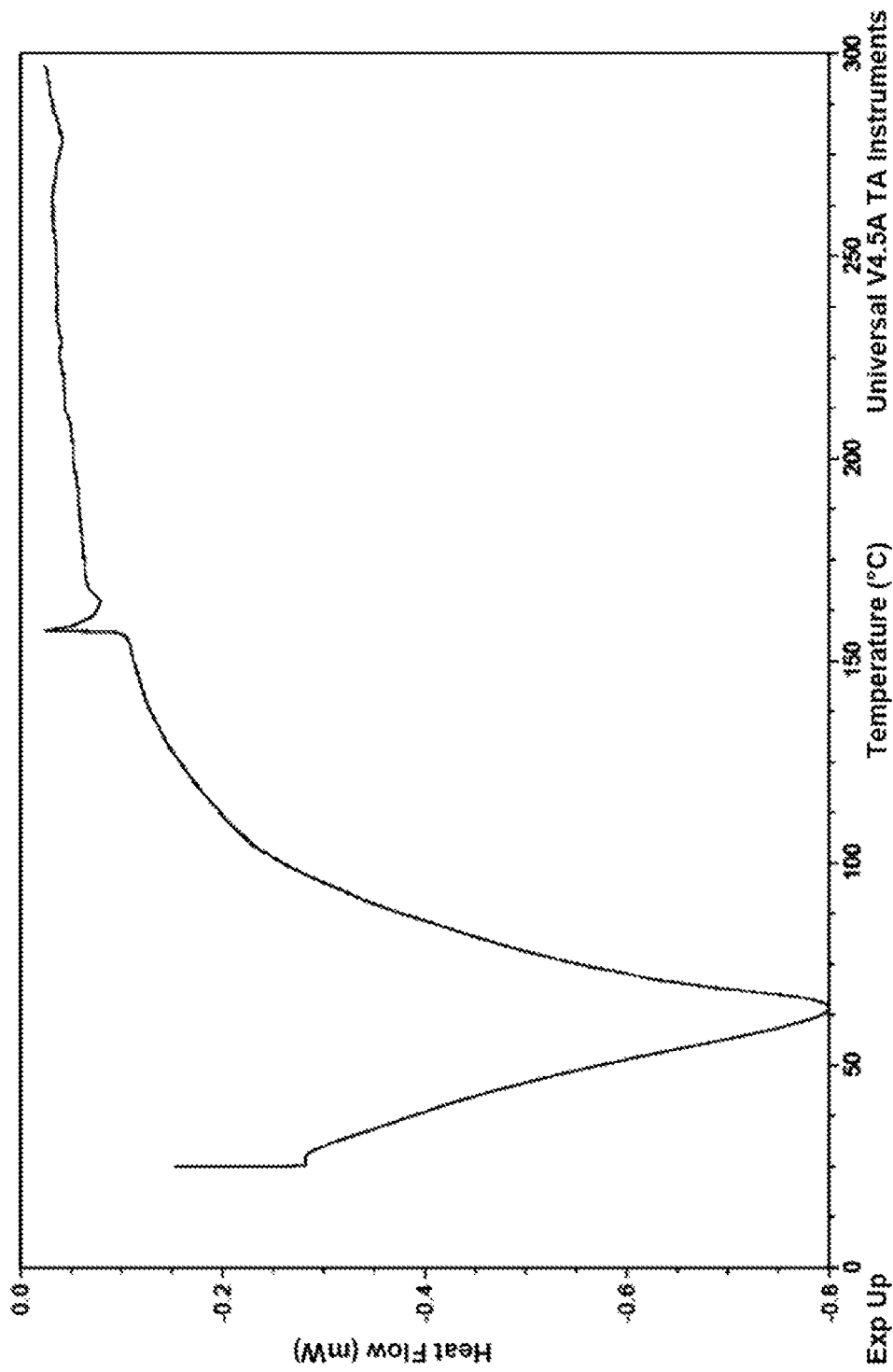
FIG. 3 shows the profile determined by the differential scanning calorimeter method (DSC), of polymorphic form #1 of sodium benzoate from Example 1.

In some embodiments, the sodium benzoate compound is the polymorphic form #1 of sodium benzoate having an X-ray powder diffraction pattern at a reflection angle 2θ further comprising characteristic peaks at approximately 3.6, 5.9, 7.2, 7.5, 14.9, 15.9, 16.6, 17.6, 18.8, 20.4, 22.9, 23.7, 25.1, 25.8, 26.6, 28.1, 29.1, 29.4, 29.7, 30.2, 31.2, 31.5, 32.9, 34.2, 35.7 degrees. In some embodiments, the polymorphic form of sodium benzoate has an X-ray powder diffraction pattern substantially as depicted in FIG. 1. In some embodiments, the polymorphic form of sodium benzoate has a TGA pattern substantially as depicted in FIG. 2. In some embodiments, the polymorphic form of sodium benzoate has a DSC pattern substantially as depicted in FIG. 3.

Figure 4:
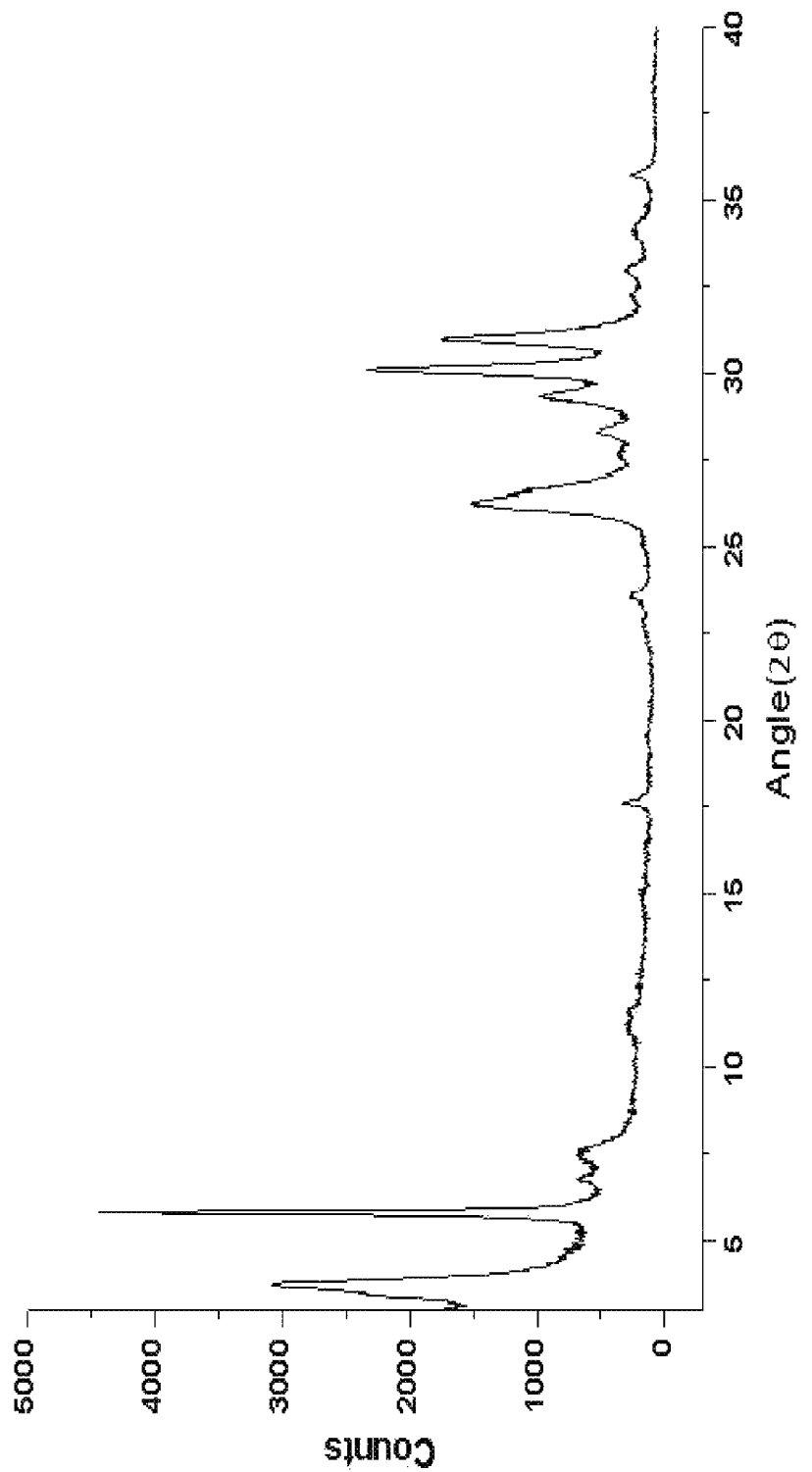
FIG. 4 shows the X-ray powder diffraction (XRPD) of polymorphic form #2 of sodium benzoate from Example 2, with peaks (°) of: 3.7, 5.9, 6.8, 7.5, 11.3, 11.6, 17.6, 22.7, 23.5, 26.2, 27.6, 28.3, 29.3; 30.2, 31.2, 32.2, 32.9, 34.0, 35.7.
Figure 5:
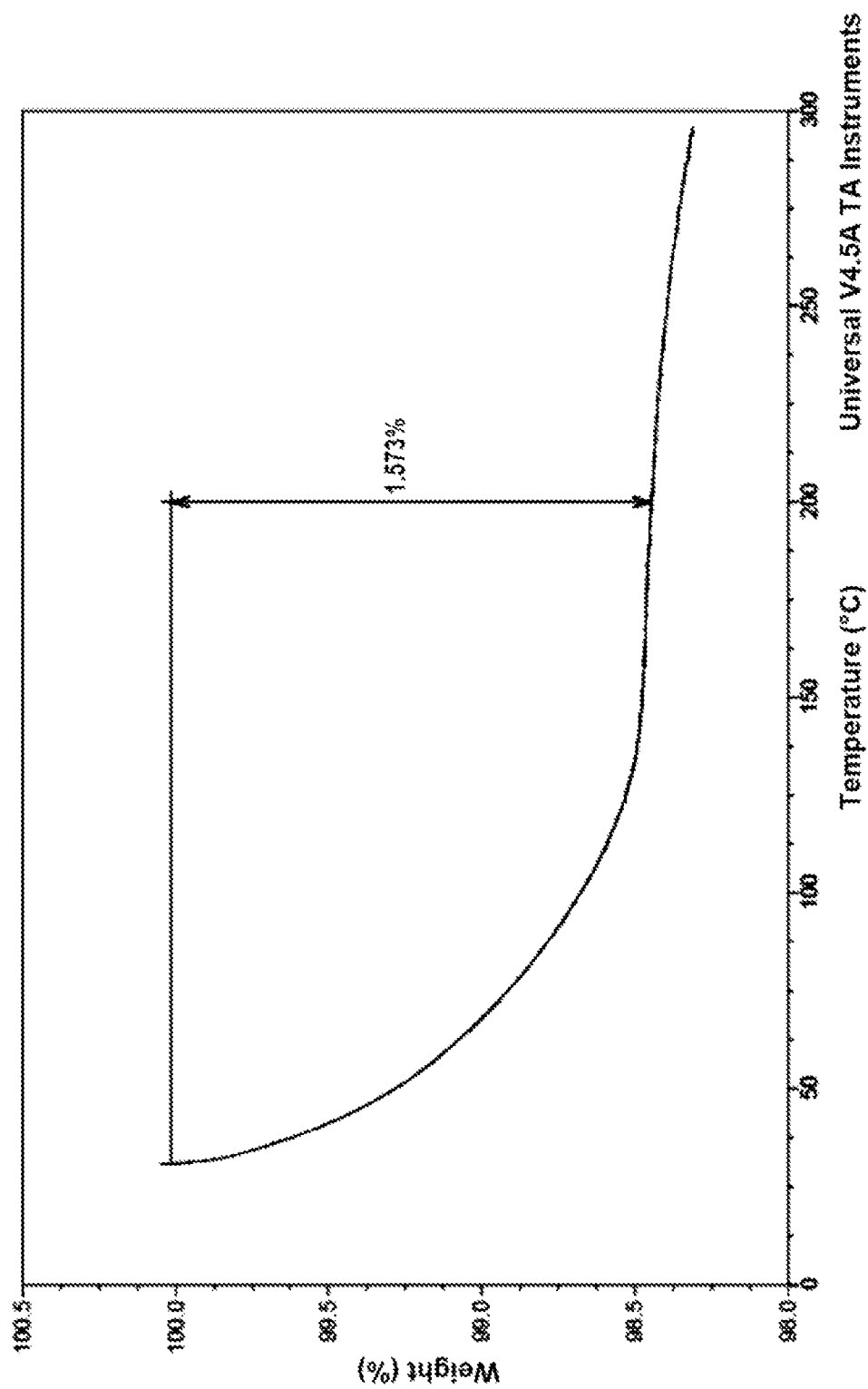
FIG. 5 shows the Thermogravimetric Analysis (TGA) of polymorphic form #2 of sodium benzoate from Example 2.
Figure 6:
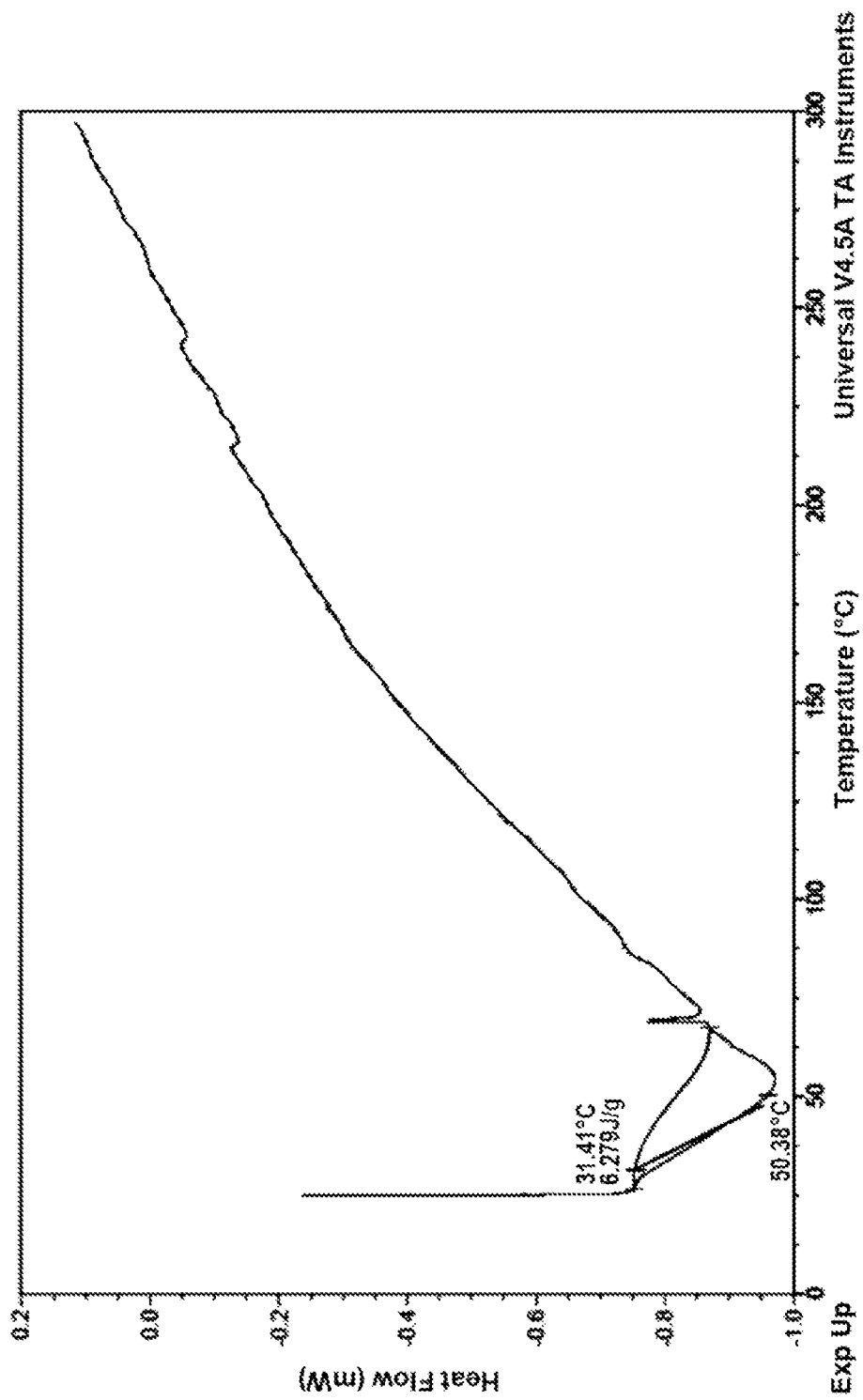
FIG. 6 shows the profile determined by the differential scanning calorimeter method (DSC), of polymorphic form #2 of sodium benzoate from Example 2.

In some embodiments, the sodium benzoate compound is the polymorphic form #2 of sodium benzoate having an X-ray powder diffraction pattern at a reflection angle 2θ further comprising characteristic peaks at approximately 3.7, 5.9, 6.8, 7.5, 11.3, 11.6, 17.6, 22.7, 23.5, 26.2, 27.6, 28.3, 29.3; 30.2, 31.2, 32.2, 32.9, 34.0, 35.7 degrees. In some embodiments, the polymorphic form of sodium benzoate has an X-ray powder diffraction pattern substantially as depicted in FIG. 4. In some embodiments, the polymorphic form of sodium benzoate has a TGA pattern substantially as depicted in FIG. 5. In some embodiments, the polymorphic form of sodium benzoate has a DSC pattern substantially as depicted in FIG. 6.

Figure 7:
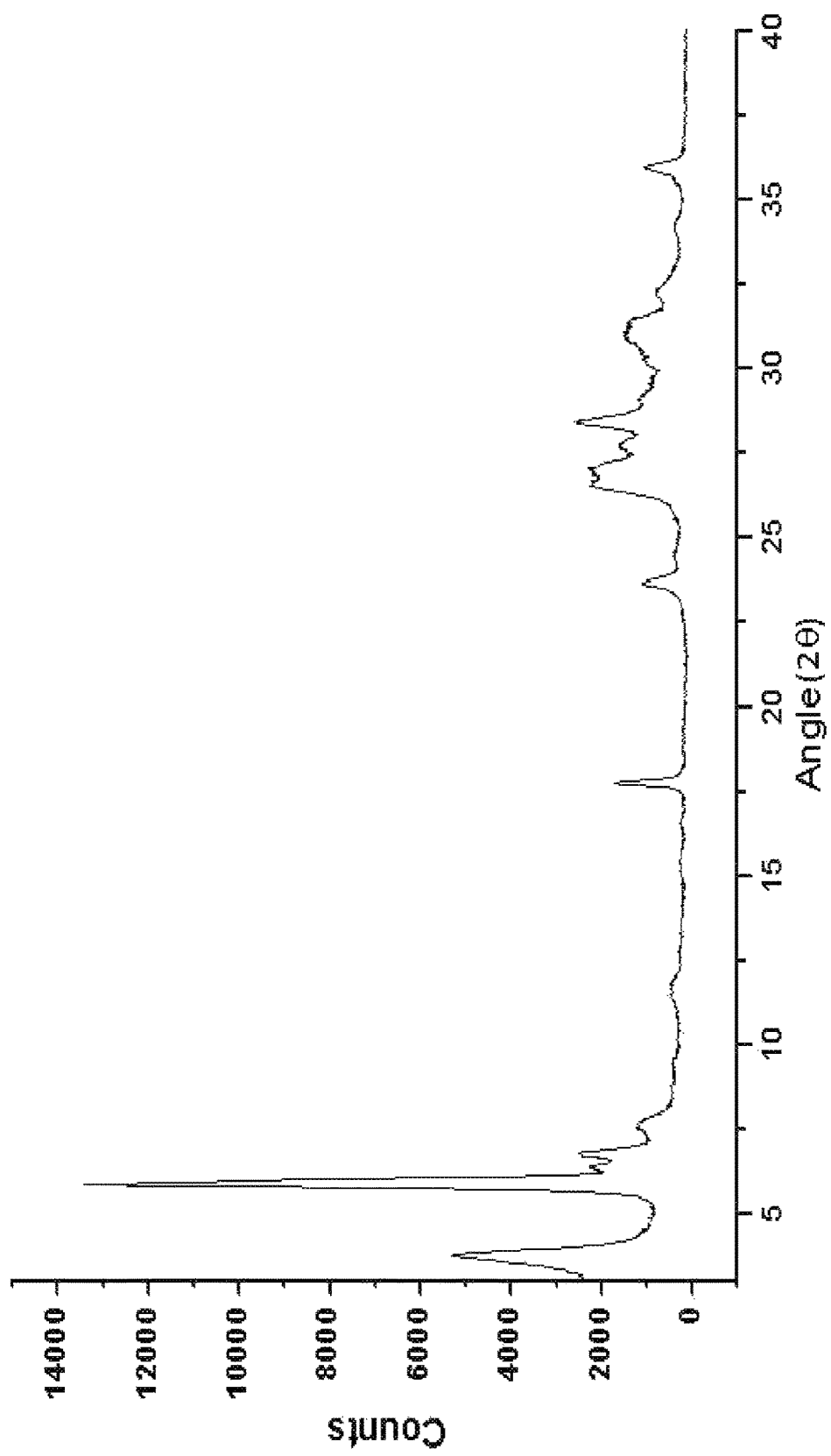
FIG. 7 shows the X-ray powder diffraction (XRPD) of polymorphic form #3 of sodium benzoate from Example 3, with peaks (°) of: 3.7, 5.9, 6.3, 6.8, 7.5, 11.7, 17.7, 23.6, 24.5, 26.5, 27.0, 27.7, 28.4, 29.0, 30.2; 31.0, 31.2, 32.3, 34.2, 35.9.
Figure 8:
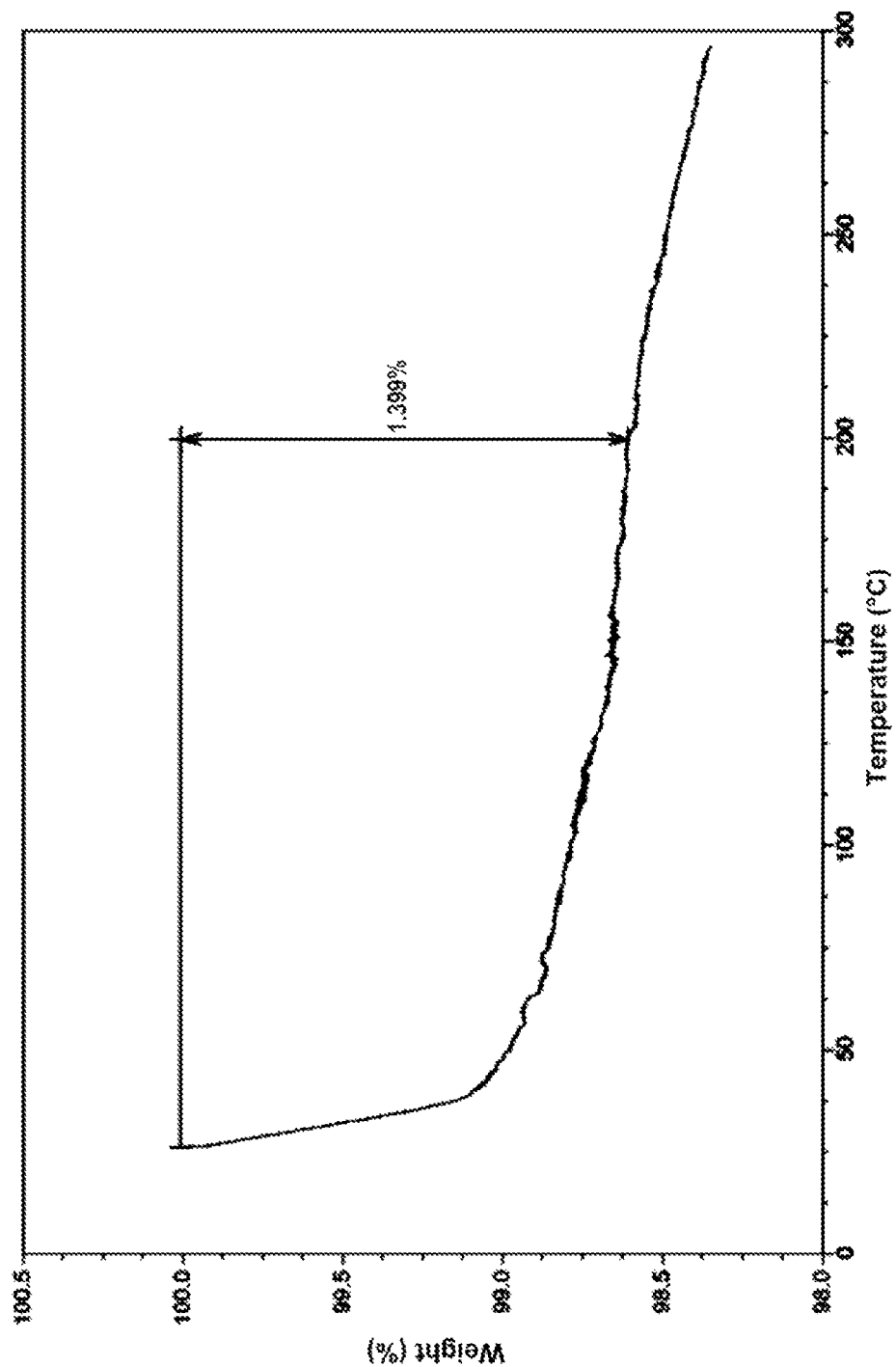
FIG. 8 shows the Thermogravimetric Analysis (TGA) of polymorphic form #3 of sodium benzoate from Example 3.
Figure 9:
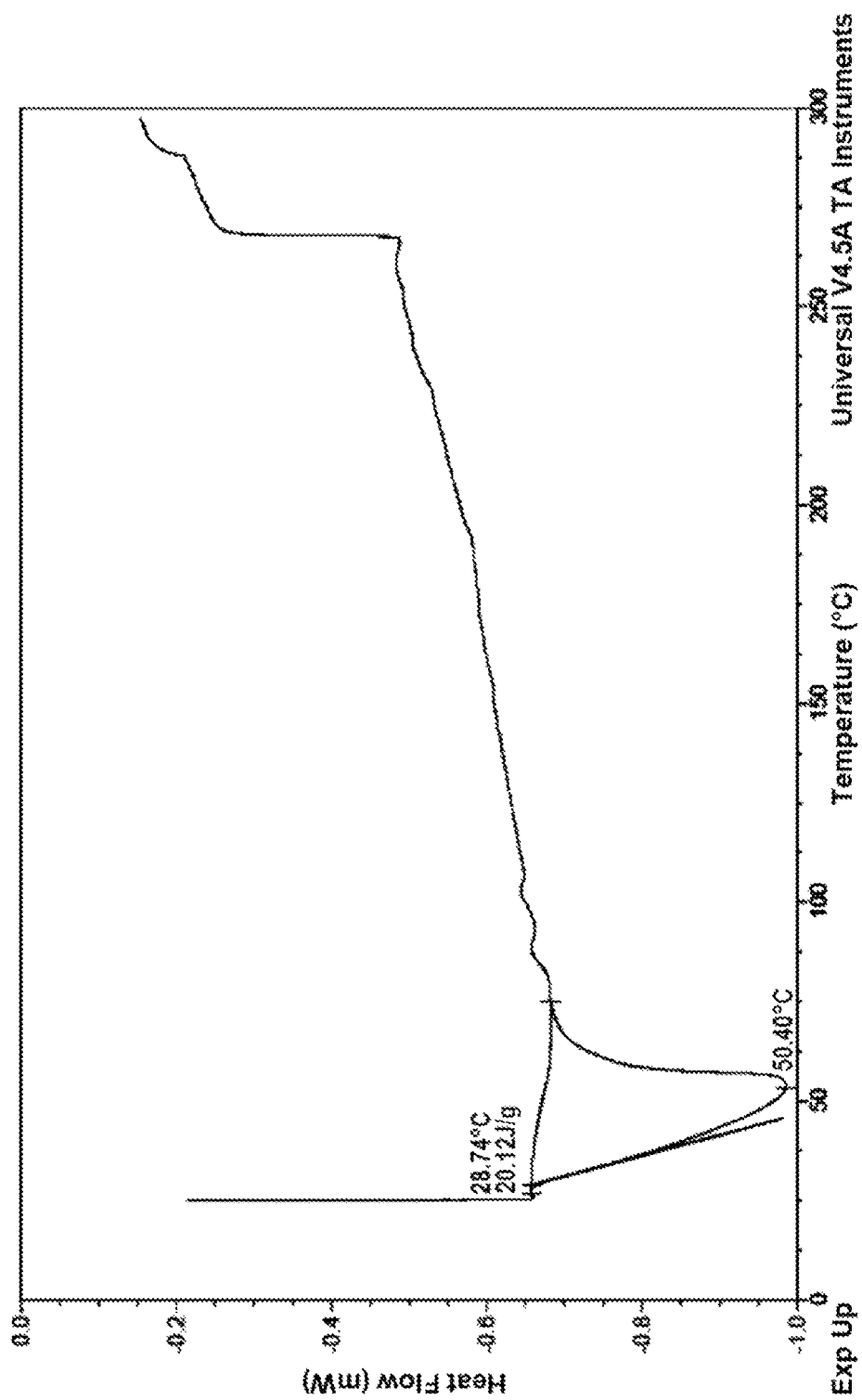
FIG. 9 shows the profile determined by the differential scanning calorimeter method (DSC), of polymorphic form #3 of sodium benzoate from Example 3.

In some embodiments, the sodium benzoate compound is the polymorphic form #3 of sodium benzoate having an X-ray powder diffraction pattern at a reflection angle 2θ further comprising characteristic peaks at approximately 3.7, 5.9, 6.3, 6.8, 7.5, 11.7, 17.7, 23.6, 24.5, 26.5, 27.0, 27.7, 28.4, 29.0, 30.2; 31.0, 31.2, 32.3, 34.2, 35.9 degrees. In some embodiments, the polymorphic form of sodium benzoate has an X-ray powder diffraction pattern substantially as depicted in FIG. 7. In some embodiments, the polymorphic form of sodium benzoate has a TGA pattern substantially as depicted in FIG. 8. In some embodiments, the polymorphic form of sodium benzoate has a DSC pattern substantially as depicted in FIG. 9.

Figure 10:
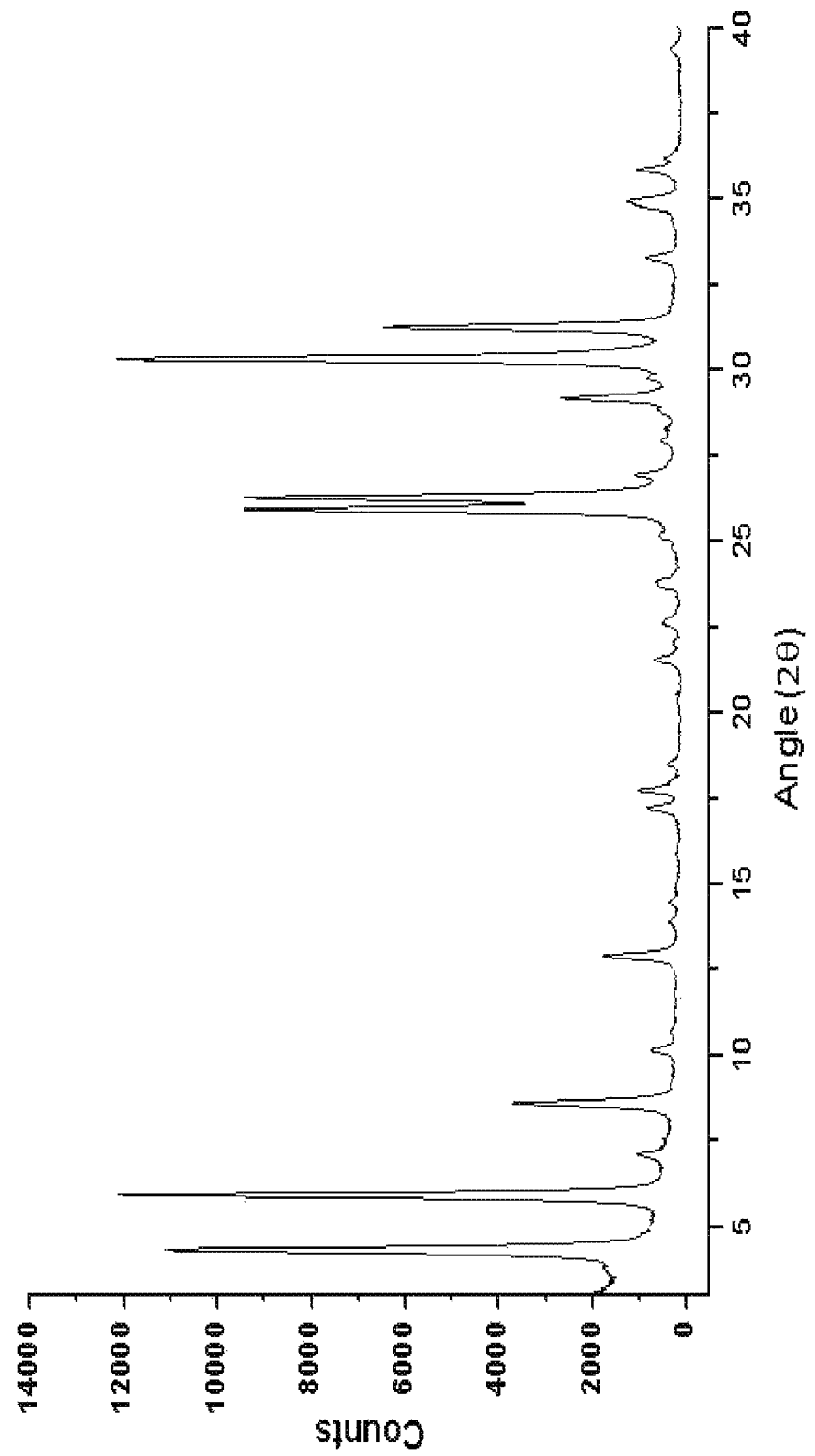
FIG. 10 shows the X-ray powder diffraction (XRPD) of polymorphic form #4 of sodium benzoate from Example 4, with peaks (°) of: 4.3, 5.9, 7.1, 8.6, 10.1, 10.7, 12.9, 13.8, 14.4, 17.2, 17.7, 18.5, 21.5, 22.0, 22.6, 23.7, 25.1, 25.9, 26.2, 26.9, 27.9, 28.2, 28.8, 29.1, 29.7, 30.2, 31.2, 33.2, 34.9, 35.8, 36.1, and 39.3.
Figure 11:
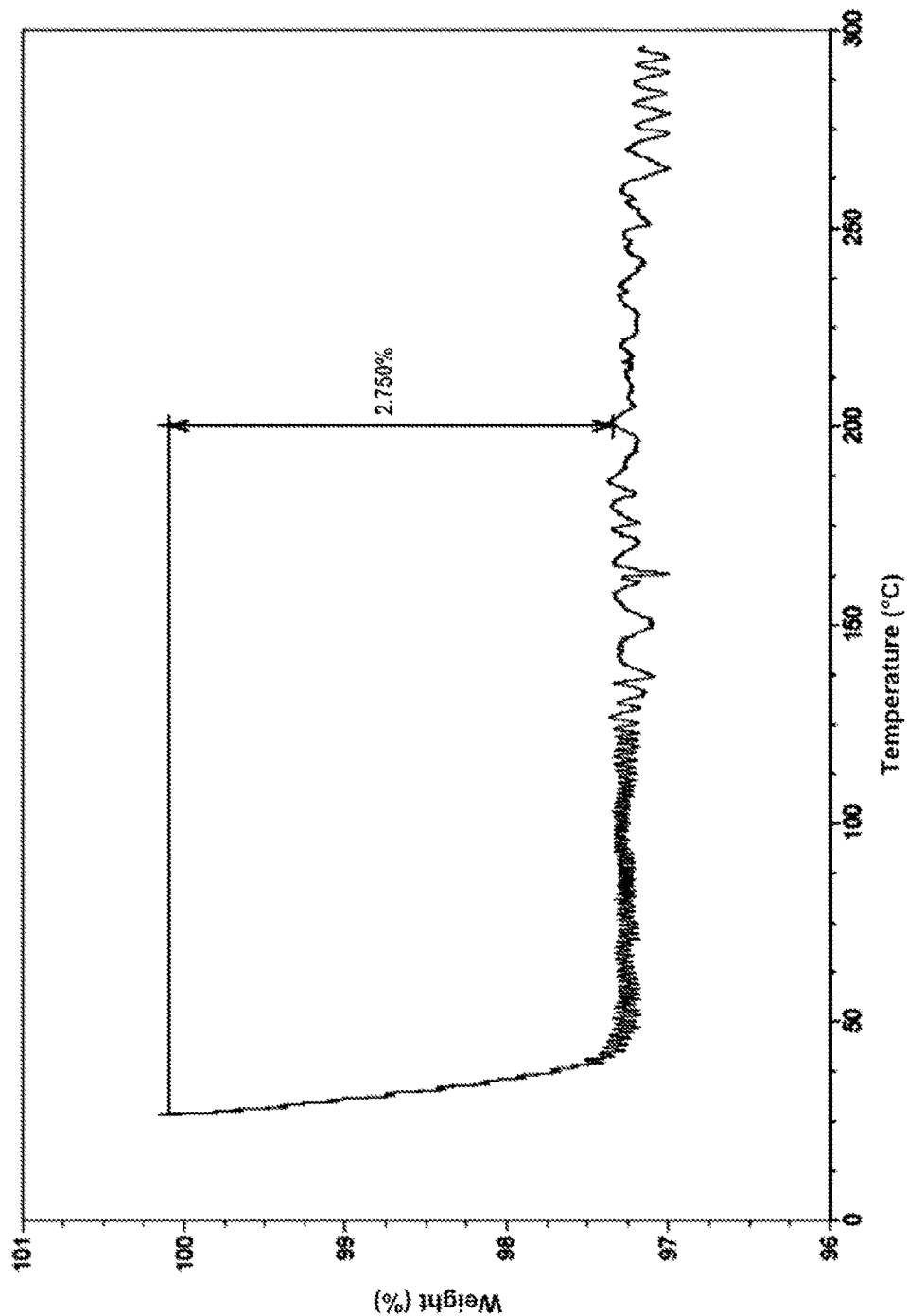
FIG. 11 shows the Thermogravimetric Analysis (TGA) of polymorphic form #4 of sodium benzoate from Example 4.
Figure 12:
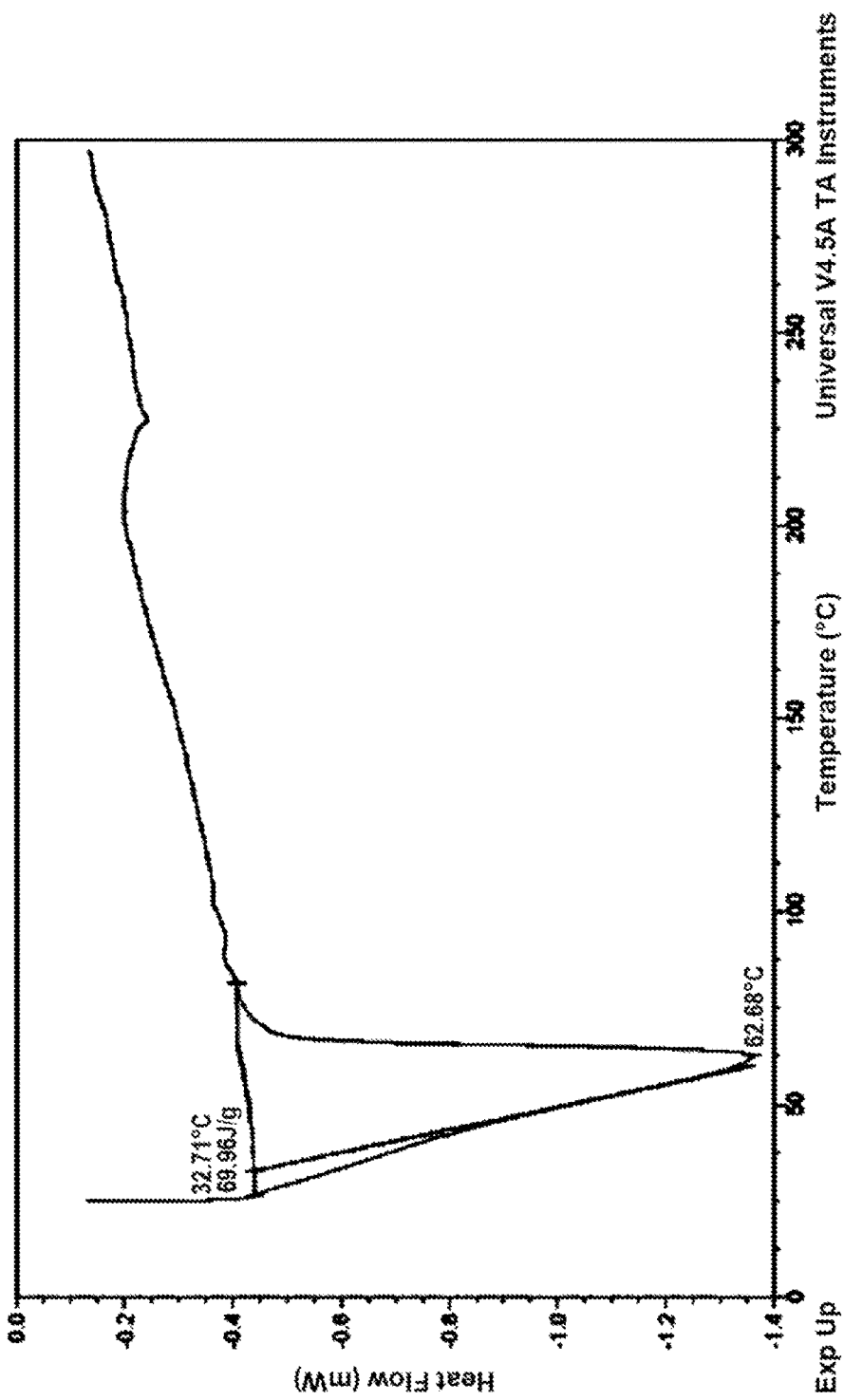
FIG. 12 shows the profile determined by the differential scanning calorimeter method (DSC), of polymorphic form #4 of sodium benzoate from Example 4.

In some embodiments, the sodium benzoate compound is the polymorphic form #4 of sodium benzoate having an X-ray powder diffraction pattern at a reflection angle 2θ further comprising characteristic peaks at approximately 4.3, 5.9, 7.1, 8.6, 10.1, 10.7, 12.9, 13.8, 14.4, 17.2, 17.7, 18.5, 21.5, 22.0, 22.6, 23.7, 25.1, 25.9, 26.2, 26.9, 27.9, 28.2, 28.8, 29.1, 29.7, 30.2, 31.2, 33.2, 34.9, 35.8, 36.1, and 39.3 degrees. In some embodiments, the polymorphic form of sodium benzoate has an X-ray powder diffraction pattern substantially as depicted in FIG. 10. In some embodiments, the polymorphic form of sodium benzoate has a TGA pattern substantially as depicted in FIG. 11. In some embodiments, the polymorphic form of sodium benzoate has a DSC pattern substantially as depicted in FIG. 12.

Any of the polymorphic forms of sodium benzoate described herein has a chemical purity of about 95%, 97%, 98%, 99%, 99.5%, 99.9% or higher, which can be determined by a conventional method, for example, HPLC or $^1$H Nuclear Magnetic Resonance ($^1$H-NMR) spectroscopy. In some embodiments, the polymorphic form of sodium benzoate described herein contains less than 10%, preferably less than 5%, preferably less than 1%, preferably less than 0.5%, and most preferably less than 0.1% of sodium benzoate in other polymorphic or amorphous forms (as measured by XRPD or DSC).

In certain embodiments, the pharmaceutical composition described herein further comprises one or more pharmaceutically acceptable excipients. In certain embodiments, the pharmaceutical composition comprises 50 to 1000 mg of sodium benzoate compound, 25 to 300 mg of clozapine, and one or more pharmaceutically acceptable excipients. In certain embodiments, the pharmaceutical composition comprises 500 mg of sodium benzoate compound, 200 to 300 mg of clozapine, and one or more pharmaceutically acceptable excipients.

In certain embodiments, the ratio of the sodium benzoate compound to clozapine is about 1:10 to about 1000:1, about 1:10 to about 900:1, about 1:10 to about 800:1, about 1:10 to about 600:1, about 1:10 to about 500:1, about 1:10 to about 400:1, about 1:10 to about 200:1, about 1:10 to about 100:1, about 1:10 to about 75:1, about 1:10 to about 50:1, about 1:10 to about 25:1, about 1:10 to about 10:1, about 1:10 to about 5:1, about 1:10 to about 1:2, about 1:10 to about 1:5, or about 1:10 to about 1:8 by weight. In certain embodiments, the ratio of the sodium benzoate compound to clozapine is about 20:1, about 5:1, about 2.5:1, or about 1.67:1 by weight.

In certain embodiments, the sodium benzoate compound described herein is provided in an effective amount in the pharmaceutical composition. In certain embodiments, clozapine is provided in an effective amount in the pharmaceutical composition. In certain embodiments, the effective amount is a therapeutically effective amount (e.g., amount effective for treating and/or reducing the risk for a neuropsychiatric disorder in a subject in need thereof). In certain embodiments, the effective amount is a prophylactically effective amount (e.g., amount effective for preventing a neuropsychiatric disorder in a subject in need thereof).

Pharmaceutical compositions described herein can be prepared by any method known in the art of pharmacology. In general, such preparatory methods include bringing the sodium benzoate compound described herein and clozapine (i.e., the "active ingredients") into association with a carrier or excipient, and/or one or more other accessory ingredients, and then, if necessary and/or desirable, shaping, and/or packaging the product into a desired single- or multi-dose unit.

Pharmaceutical compositions can be prepared, packaged, and/or sold in bulk, as a single unit dose, and/or as a plurality of single unit doses. A "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage, such as one-half or one-third of such a dosage.

Relative amounts of the active ingredients and/or the pharmaceutically acceptable excipient in a pharmaceutical composition described herein will vary, depending upon the identity, size, and/or condition of the subject treated and further depending upon the route by which the composition is to be administered. The composition may comprise between 0.1% and 100% (w/w) of active ingredients.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

In certain embodiments, the one or more pharmaceutical acceptable excipients comprised in the pharmaceutical composition are selected from boric acid, sodium alginate, sodium citrate, sodium hyaluronate, chitosan, magnesium stearate, sodium stearyl fumarate, colloidal silicon dioxide, talc, sodium starch glycolate, croscarmellose crospovidone and tannic acid.

In particular embodiments, the pharmaceutical compositions disclosed herein comprise excipients in a total amount of about 60% (w/w). In some examples, the excipients comprise sodium alginate, sodium citrate, or a combination thereof. The daily intake of sodium alginate may be 150 mg/kg-600 mg/kg, for example, 200 mg/kg or 500 mg/kg. The daily intake of sodium citrate may be 200 mg/kg to 500 mg/kg, for example, 400 mg/kg. In some examples, the excipients may further comprise magnesium stearate, sodium starch glycolate (SSG), or a combination thereof. The amount of magnesium stearate in the composition can be 2-10% by weight (e.g., 5% or 100 mg in total 1,000 mg of a composition). The amount of SSG in the composition can be 5-15% by weight (e.g., 10% or 200 mg in total 1,000 mg of a composition).

In certain embodiments, the pharmaceutical composition disclosed herein comprises 50 to 1000 mg of sodium benzoate (e.g., 100 to 800 mg, 200 to 600 mg, or 300 to 500 mg), 25-300 mg of clozapine (e.g., 50 to 200 mg, 100 to 150 mg, or 150 to 300 mg), 50-500 mg of sodium alginate (e.g., 100 to 400 mg, 200 to 300 mg, or 250 to 400 mg), 50-400 mg of sodium citrate (e.g., 100-300 mg, 150-250 mg, or 200-300 mg), 5-100 mg of magnesium stearate (e.g., 10-80 mg, 25-70 mg, 40-60 mg, or 50-100 mg), and 80-200 mg of sodium starch glycolate (e.g., 100-150 mg). In certain embodiments, the pharmaceutical composition disclosed herein comprises 125 to 500 mg of sodium benzoate, 25-300 mg of clozapine, 50-500 mg of sodium alginate, 50-400 mg of sodium citrate, 5-100 mg of magnesium stearate, and 80-200 mg of sodium starch glycolate.

In certain embodiments, the pharmaceutical composition disclosed herein comprises 50 to 1000 mg of sodium benzoate, 25-300 mg of clozapine, 50-200 mg of sodium alginate, 50-400 mg of sodium citrate, 5-100 mg of magnesium stearate, and 80-200 mg of sodium starch glycolate. In certain embodiments, the pharmaceutical composition disclosed herein comprises 125 to 500 mg of sodium benzoate, 25-300 mg of clozapine, 50-200 mg of sodium alginate, 50-400 mg of sodium citrate, 5-100 mg of magnesium stearate, and 80-200 mg of sodium starch glycolate.

In certain embodiments, the pharmaceutical composition disclosed herein comprises 50 to 1000 mg of sodium benzoate, 25-300 mg of clozapine, 50-70 mg of sodium alginate, 50-70 mg of sodium citrate, 5-15 mg of magnesium stearate, and 80-100 mg of sodium starch glycolate. In certain embodiments, the pharmaceutical composition disclosed herein comprises 125 to 500 mg of sodium benzoate, 25-300 mg of clozapine, 50-70 mg of sodium alginate, 50-70 mg of sodium citrate, 5-15 mg of magnesium stearate, and 80-100 mg of sodium starch glycolate.

Solid dosage forms for oral administration include capsules, tablets, dragees, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, sodium starch glycolate (SSG), croscarmellose, crospovidone, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as magnesium stearate, colloidal silicon dioxide, talc, calcium stearate, solid polyethylene glycols, sodium lauryl sulfate, and mixtures thereof. In the case of capsules, tablets, and pills, the dosage form may include a buffering agent such as sodium citrate, and chitosan. In addition, the pharmaceutically acceptable excipient described herein can be single species or a mixture of multiple species of tannic acid, or a pharmaceutically acceptable salt thereof.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the digestive tract, optionally, in a delayed manner. Examples of encapsulating compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings, and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the digestive tract, optionally, in a delayed manner. Examples of encapsulating agents which can be used include, but are not limited to, polymeric substances and waxes.

Although the descriptions of pharmaceutical compositions provided herein are mainly directed to pharmaceutical compositions which are suitable for administration to humans, such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

The active ingredients including the sodium benzoate compound and clozapine provided herein are typically formulated in dosage unit form for ease of administration and uniformity of dosage. It will be understood, however, that the total daily usage of the pharmaceutical compositions described herein will be decided by a physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex, and diet of the subject; the time of administration, route of administration, and rate of excretion of the specific active ingredient employed; the duration of the treatment; drugs used in combination or coincidental with the specific active ingredient employed; and like factors well known in the medical arts.

Also encompassed by the disclosure are kits (e.g., pharmaceutical packs). The kits provided may comprise the pharmaceutical composition described herein and a container (e.g., a vial, ampule, bottle, syringe, and/or dispenser package, or other suitable container). In some embodiments, provided kits may optionally further include a second container comprising at least one additional pharmaceutical excipient for dilution or suspension of the pharmaceutical composition described herein. In some embodiments, the pharmaceutical composition described herein provided in the first container and the one or more additional pharmaceutical excipient provided in the second container are combined to form one unit dosage form.

In certain embodiments, a kit described herein includes a first container comprising the pharmaceutical composition described herein. In certain embodiments, a kit described herein is useful in preventing, treating and/or reducing the risk for a neuropsychiatric disorder in a subject in need thereof.

In certain embodiments, a kit described herein further includes instructions for using the pharmaceutical composition included in the kit. A kit described herein may also include information as required by a regulatory agency such as the U.S. Food and Drug Administration (FDA). In certain embodiments, the information included in the kits is prescribing information. In certain embodiments, the kits and instructions provide for preventing, treating and/or reducing the risk for a neuropsychiatric disorder in a subject in need thereof. A kit described herein may include one or more additional pharmaceutical agents described herein as a separate composition.

Methods of Treatment

The present disclosure provides a method of treating and/or reducing the risk for a neuropsychiatric disorder, in a subject in need thereof, the method comprising administering to the subject a pharmaceutical composition comprising an effective amount (e.g., therapeutically effective amount) of a sodium benzoate compound described herein and an effective amount (e.g., therapeutically effective amount) of clozapine.

Another aspect of the present disclosure relates to methods of preventing a neuropsychiatric disorder in a subject in need thereof, the methods comprising administering to the subject a pharmaceutical composition comprising an effective amount (e.g., prophylactically effective amount) of a sodium benzoate compound described herein and an effective amount (e.g., prophylactically effective amount) of clozapine.

The compositions described herein are useful in treating and/or preventing neuropsychiatric disorders. In certain embodiments, the neuropsychiatric disorder is schizophrenia. In certain embodiments, the neuropsychiatric disorder is a psychotic disorder. In certain embodiments, the neuropsychiatric disorder is Alzheimer's disease. In certain embodiments, the neuropsychiatric disorder is dementia including frontotemporal dementia. In certain embodiments, the neuropsychiatric disorder is mild cognitive impairment. In certain embodiments, the neuropsychiatric disorder is benign forgetfulness. In certain embodiments, the neuropsychiatric disorder is closed head injury. In certain embodiments, the neuropsychiatric disorder is autistic spectrum disorder including Asperger's disorder. In certain embodiments, the neuropsychiatric disorder is an attention deficit hyperactivity disorder. In certain embodiments, the neuropsychiatric disorder is obsessive compulsive disorder. In certain embodiments, the neuropsychiatric disorder is a tic disorder. In certain embodiments, the neuropsychiatric disorder is a childhood learning disorder. In certain embodiments, the neuropsychiatric disorder is premenstrual syndrome. In certain embodiments, the neuropsychiatric disorder is depression, including dysthymia and bereavement. In certain embodiments, the neuropsychiatric disorder is suicidal ideation and/or behaviors. In certain embodiments, the neuropsychiatric disorder is bipolar disorder including bipolar I and II disorders. In certain embodiments, the neuropsychiatric disorder is an anxiety disorder including panic and phobic disorders. In certain embodiments, the neuropsychiatric disorder is post-traumatic stress disorder. In certain embodiments, the neuropsychiatric disorder is chronic pain. In certain embodiments, the neuropsychiatric disorder is an eating disorder including bulimia and anorexia. In certain embodiments, the neuropsychiatric disorder is an addiction disorder including substance dependence or abuse. In certain embodiments, the neuropsychiatric disorder is a personality disorder. In certain embodiments, the neuropsychiatric disorder is Parkinson's disorder. In certain embodiments, the neuropsychiatric disorder is Huntington's disorder. In certain embodiments, the neuropsychiatric disorder is multiple sclerosis. In certain embodiments, the neuropsychiatric disorder is amyotrophic lateral sclerosis.

In certain embodiments, the method described herein further includes administering to the subject an additional pharmaceutical agent. In certain embodiments, the method described herein further includes contacting the biological sample with an additional pharmaceutical agent. In certain embodiments, the method described herein further includes contacting the tissue with an additional pharmaceutical agent. In certain embodiments, the method described herein further includes contacting the cell with an additional pharmaceutical agent.

The pharmaceutical compositions provided herein can be administered by any systemic or topical route, including enteral (e.g., oral), parenteral, intravenous, intramuscular, intra-arterial, intramedullary, intrathecal, subcutaneous, intraventricular, transdermal, interdermal, subcutaneous, intradermal, rectal, intravaginal, intraperitoneal, topical (as by powders, ointments, creams, and/or drops). Specifically contemplated routes are oral administration, intravenous administration (e.g., systemic intravenous injection), regional administration via blood and/or lymph supply, and/or direct administration to an affected site. In general, the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of the active ingredients described herein (e.g. the sodium benzoate compound described herein and/or clozapine) required to achieve an effective amount will vary from subject to subject, depending, for example, on species, age, and general condition of a subject, severity of the side effects or disorder, identity of the particular polymorph, mode of administration, and the like. An effective amount may be included in a single dose (e.g., single oral dose) or multiple doses (e.g., multiple oral doses). In certain embodiments, when multiple doses are administered to a subject or applied to a biological sample, tissue, or cell, any two doses of the multiple doses include different or substantially the same amounts of any of the active ingredients described herein. In certain embodiments, when multiple doses are administered to a subject or applied to a biological sample, tissue, or cell, the frequency of administering the multiple doses to the subject or applying the multiple doses to the tissue or cell is three doses a day, two doses a day, one dose a day, one dose every other day, one dose every third day, one dose every week, one dose every other week, one dose monthly or one dose every other month. In certain embodiments, the frequency of administering the multiple doses to the subject or applying the multiple doses to the tissue or cell is one dose per day. In certain embodiments, the frequency of administering the multiple doses to the subject or applying the multiple doses to the tissue or cell is two doses per day. In certain embodiments, when multiple doses are administered to a subject or applied to a biological sample, tissue, or cell, the duration between the first dose and last dose of the multiple doses is one day, two days, four days, one week, two weeks, three weeks, one month, two months, three months, four months, six months, nine months, one year, two years, three years, four years, five years, seven years, ten years, fifteen years, twenty years, or the lifetime of the subject, biological sample, tissue, or cell. In certain embodiments, the duration between the first dose and last dose of the multiple doses is three months, six months, or one year. In certain embodiments, the duration between the first dose and last dose of the multiple doses is the lifetime of the subject, biological sample, tissue, or cell. In certain embodiments, a dose (e.g., a single dose, or any dose of multiple doses) described herein includes independently between 1 mg and 3 mg, between 3 mg and 10 mg, between 10 mg and 30 mg, between 30 mg and 100 mg, between 100 mg and 300 mg, between 300 mg and 1,000 mg, or between 1 g and 10 g, inclusive, of any of the active ingredients described herein. In certain embodiments, a dose described herein includes independently between 3 mg and 10 mg, inclusive, of any of the active ingredients described herein. In certain embodiments, a dose described herein includes independently between 10 mg and 30 mg, inclusive, of any of the active ingredients described herein. In certain embodiments, a dose described herein includes independently between 30 mg and 100 mg, inclusive, of any of the active ingredients described herein. In certain embodiments, a dose described herein includes independently between 100 mg and 300 mg, inclusive, of any of the active ingredients described herein. In certain embodiments, a dose described herein includes independently between 300 mg and 1000 mg, inclusive, of any of the active ingredients described herein.

Dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

The pharmaceutical composition described herein can be administered concurrently with, prior to, or subsequent to one or more additional pharmaceutical agents, which may be useful as, e.g., combination therapies in preventing, treating and/or reducing the risk for a neuropsychiatric disorder in a subject. Pharmaceutical agents include therapeutically active agents. Pharmaceutical agents also include prophylactically active agents. Pharmaceutical agents include small organic molecules such as drug compounds or polymorphic forms thereof (e.g., compounds approved for human or veterinary use by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, antibodies, small molecules linked to proteins such as antibodies, glycoproteins, steroids, nucleic acids, DNAs, RNAs, nucleotides, nucleosides, oligonucleotides, antisense oligonucleotides, lipids, hormones, vitamins, and cells. In certain embodiments, the additional pharmaceutical agent is a pharmaceutical agent useful in preventing, treating and/or reducing the risk for a neuropsychiatric disorder in a subject. In certain embodiments, the additional pharmaceutical agent is a pharmaceutical agent approved by a regulatory agency (e.g., the US FDA, EMA, China FDA) for preventing, treating and/or reducing the risk for a neuropsychiatric disorder in a subject. In certain embodiments, the additional pharmaceutical agent is a neuropharmaceutical selected from the group consisting of cariprazine, brexpiprazole, iloperidone, pimavanserin, luradisone, butyrophenone, phenothiazine, fluphenazine, perphenazine, prochlorperazine, thioridazine, trifluoperazine, mesoridazine, promazine, triflupromazine, levomepromazine, promethazine, thioxanthene, chlorprothixene, flupenthixol, thiothixene, zuclopenthixol, clozapine, olanzapine, risperidone, quetiapine, ziprasidone, amisulpride, asenapine, paliperidone, aripiprazole, lamotrigine, tetrabenazine, cannabidiol, LY2140023, droperidol, pimozide, butaperazine, carphenazine, eemoxipride, piperacetazine, sulpiride, acamprosate, tetrabenazine, vilazodone, levomilnacipran, vortioxetine fluoxetine, paroxetine, escitalopram, citalopram, sertraline, fluvoxamine, venlafaxine, milnacipram, duloxetine, mirtazapine, mianserin, reboxetine, bupropion, amitriptyline, nortriptiline, protriptyline, desipramine, trimipramine, amoxapine, clomipramine, desipramine, doxepin, isocarboxazid, tranylcypromine, selegiline, trazodone, nefazodone, phenelzine, lamatrogine, lithium, topiramate, gabapentin, carbamazepine, oxacarbazepine, valporate, maprotiline, mirtazapine, brofaromine, gepirone, moclobemide, isoniazid, iproniazid, a statin, an amphetamine, modafinil, desoxyn, methamphetamine, cocaine, arecoline, dexmethylphenidate, dextroamphetamine, methylphenidate, lisdexamfetamine dimesylate, mixed salts amphetamine, atomoxetine, clonidine hydrochloride, guanfacine hydrochloride, arecoline, pemoline, donepezil, tacrine, rivastigmine, memantine, physostigmine, lithium salts, nicotine, arecoline, huperzine alpha, riluzole, vitamin C, vitamin E, carotenoids, tannic acid, and Ginkgo Biloba extract.

Each additional pharmaceutical agent may be administered at a dose and/or on a time schedule determined for that pharmaceutical agent. The additional pharmaceutical agents may also be administered together with each other and/or with the pharmaceutical composition described herein in a single dose or administered separately in different doses. The particular combination to employ in a regimen will take into account compatibility of the active ingredients of the pharmaceutical composition described herein with the additional pharmaceutical agent(s) and/or the desired therapeutic and/or prophylactic effect to be achieved. In general, it is expected that the additional pharmaceutical agent(s) in combination be utilized at levels that do not exceed the levels at which they are utilized individually. In some embodiments, the levels utilized in combination will be lower than those utilized individually.

In certain embodiments, the additional pharmaceutical agent is an agent for preventing, treating and/or reducing the risk for a neuropsychiatric disorder. In certain embodiments, the pharmaceutical compositions described herein can be administered in combination with a therapy for preventing, treating and/or reducing the risk for a neuropsychiatric disorder.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Preparation of Polymorphic Form #1 of Sodium Benzoate 199.93 mg of sodium benzoate was placed in a flask and 4 mL of methanol was added to dissolve the sodium benzoate. Unless otherwise indicated, commercially available sodium benzoate was purchased from Merck, Formosa Laboratories Inc., or Sigma Aldrich, and solvents were purchased from vendors such as Acros, Merck, and Sigma Aldrich. The solution thus formed was kept stirring for 10 min and then filtered to remove any insoluble ingredients. The filtrate was evaporated by rotary evaporation to form solid sodium benzoate in a polymorphic form. The solid obtained was analyzed by XRPD, TGA, and DSC as described below.

Thermogravimetric Analysis (TGA).

Total weight loss was obtained on a TA Instrument TGA Model Q500. The sample was heated in an opened aluminum pan at the heating rate of 10° C./min up to the final temperature.

Differential Scanning calorimetry.

Thermal analysis was performed using a TA Instrument DSC Model Q200. The sample was heated in an aluminum pan at the heating rate of 10° C./min with 50 mL/min nitrogen purge up to the final temperature.

X-Ray Powder Diffractometry.

The solid samples were determined by X-ray powder diffractometer (Bruker D8 advance) equipped with LynxEye detector. The instrument parameters were listed below. Scan: 3° (2θ) to 40° (2θ); Increment: 0.02° (2θ); Scan speed: 0.1-0.3 sec/step; Voltage: 40 KV; Current: 40 mA; Rotation: On; Sample hold: Zero-background sample holder.

The results obtained from the TGA, DSC and X-ray powder diffractometry assays are provided in FIGS. 1-3. This polymorphic form of sodium benzoate was named as polymorphic form #1 of sodium benzoate.

Example 2: Preparation of Polymorphic Form #2 of Sodium Benzoate 2.005 mg of commercially available sodium benzoate was placed in a round bottom flask followed by the addition of 150 mL of acetonitrile. The suspension thus formed was kept stirring for 2 days and filtered to collect solid sodium benzoate thus formed. The solid sodium benzoate, in a polymorphic form, was also analyzed by XRPD, TGA, and DSC and the results are shown in FIGS. 4-6. This polymorphic form of sodium benzoate was named as polymorphic form #2 of sodium benzoate.

Example 3: Preparation of Polymorphic Form #3 of Sodium Benzoate 2.006 g of commercially available sodium benzoate was placed in a round bottom flask and 150 mL of isobutanol was added. The suspension thus formed was kept stirring for 6 days and filtered afterwards. The solid sodium benzoate thus formed was collected and analyzed by XRPD, TGA, and DSC. The results are shown in FIGS. 7-9. This polymorphic form of sodium benzoate was named as polymorphic form #3 of sodium benzoate.

Example 4, Preparation of Polymorphic Form #4 of Sodium Benzoate 2.182 g of commercially available sodium benzoate was placed in a round bottom flask followed by the addition of 4 mL of water. 20 mL of isopropyl alcohol was then added gradually and the resulting suspension was kept stirring for 3 days and filtered to collect the solid thus formed. The solid collected was analyzed by XRPD, TGA, and DSC. The results are shown in FIGS. 10-12. This polymorphic form of sodium benzoate was named as polymorphic form #4 of sodium benzoate. The following experiments were conducted with the polymorphic form #4 of sodium benzoate unless otherwise indicated.

In XRPD patterns, the polymorphic forms #1-4 had three characteristic peaks in common at a reflection angle 20 of about 5.9, 30.2, and 31.2 degrees.

Example 5: Alternative Preparation of Polymorphic Form #4 of Sodium Benzoate 1-2 mg of either one of the new polymorphic forms #1, 2 or 3 disclosed herein was slurried in 0.5 mL of acetonitrile with approximately 6% of water to allow formation of the polymorphic form #4. It was thus demonstrated that among all new polymorphic forms afforded, polymorphic form #4 was the most thermodynamically stable. According to the XRPD pattern, the crystalline sodium benzoate obtained in this example is the same as the polymorphic form #4 of sodium benzoate obtained in Example 4.

Example 6: Scale-up Preparation of Polymorphic Form #4 of Sodium Benzoate 50 g of commercially available sodium benzoate (purchased from Merck) was placed in a round bottom flask followed by the addition of 92 mL of water. 688 mL of isopropyl alcohol was slowly added and the resulting suspension was kept stirring with an overhead stirrer for 4 days and filtered to collect 22.3 g of the solid. According to the XRPD pattern, the crystalline sodium benzoate obtained in this example is the same as the polymorphic form #4 of sodium benzoate obtained in Example 4.

Example 7: Solubility Test of Commercially Available Sodium Benzoate and Polymorphic Form #4 of Sodium Benzoate To around 1 g of each of the polymorphic form #4 of sodium benzoate of the invention, commercially available sodium benzoate from Merck, and commercially available sodium benzoate from Sigma Aldrich in a vial was added water till maximum solubility was reached. The results showed that the maximum water solubility of the polymorphic form #4 of sodium benzoate of the invention (666 mg/ml) was higher than that of sodium benzoate from Merck (500 mg/ml) and Sigma Aldrich (454 mg/ml).

Therefore, the solubility of the polymorphic form #4 of sodium benzoate of the invention is about 1.3 to 1.5 times higher than the commercially available sodium benzoate products.

Figure 13:
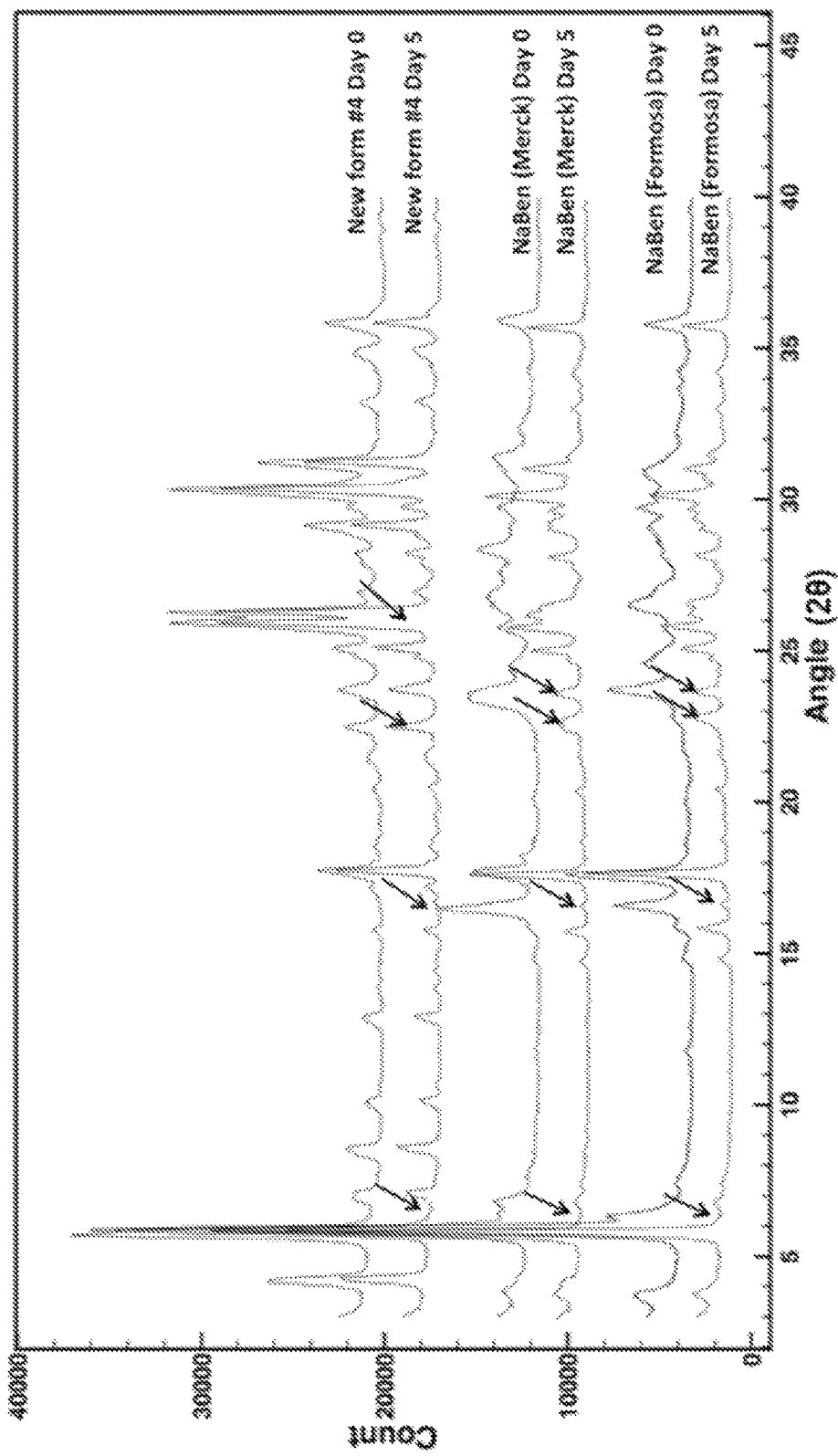
FIG. 13 shows the X-ray powder diffraction (XRPD) of sodium benzoate (NaBen) from Merck, Formosa Laboratories, and polymorphic form #4 of sodium benzoate under high humidity conditions of over 90% relative humidity for 5 days. The XRPD of the sodium benzoate from Merck and Formosa Laboratories show changes in XRPD under these high humidity conditions, but the XRPD of polymorphic form #4 of sodium benzoate from Example 5 does not show such changes in XRPD. These findings demonstrate the superior stability of polymorphic form #4 of sodium benzoate.

Example 8: Stability Tests of Commercially Available Sodium Benzoate and Polymorphic Form #4 of Sodium Benzoate 1. Stress Testing Under High Humidity Conditions 500 mg of each of commercially available sodium benzoate products from Merck and Formosa Laboratories, and the polymorphic form #4 of sodium benzoate of the invention obtained from Example 4 was stored under high humidity condition (>90% RH) at ambient temperature for 5 days and analyzed by XRPD. The results illustrated that, after 5 days, there were significant changes in the XRPD patterns with peaks at a reflection angle 20 of approximately 6.2, 16.5, and 24.5 degrees and the appearance of a new peak at 22.9 degrees of sodium benzoate from Merck and Formosa Laboratories, while no change in the XRPD pattern of the polymorphic form #4 of sodium benzoate of the invention was observed. The results are shown in FIG. 13. It was thus shown that the polymorphic form #4 of sodium benzoate of the invention was more stable than the tested commercial sodium benzoate products under high humidity condition.

Figure 14:
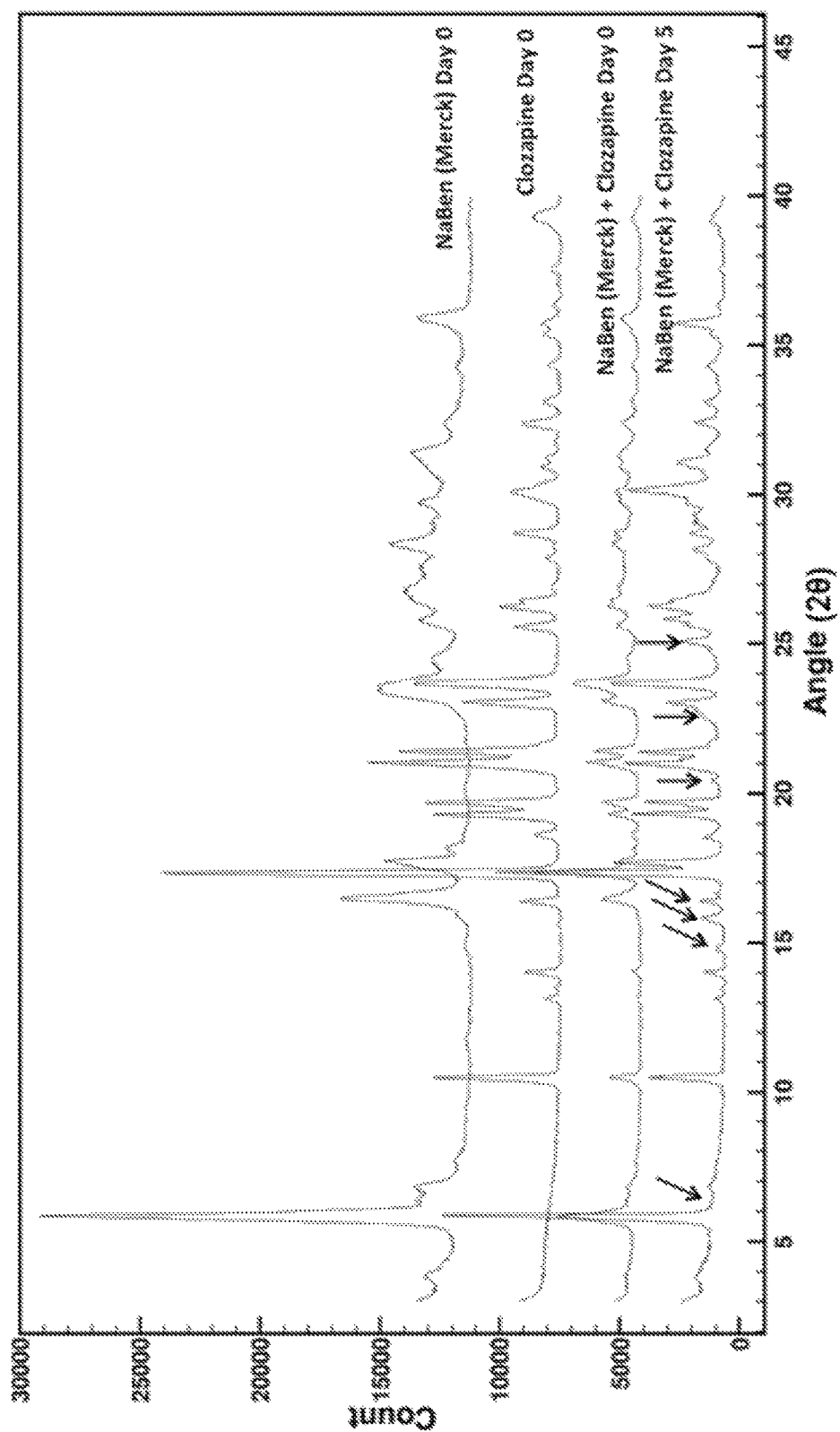
FIG. 14 shows the changes of X-ray powder diffraction (XRPD) of sodium benzoate (NaBen) from Merck combined with clozapine (300 mg) under high humidity conditions (of over 90% relative humidity) for 5 days.
Figure 15:
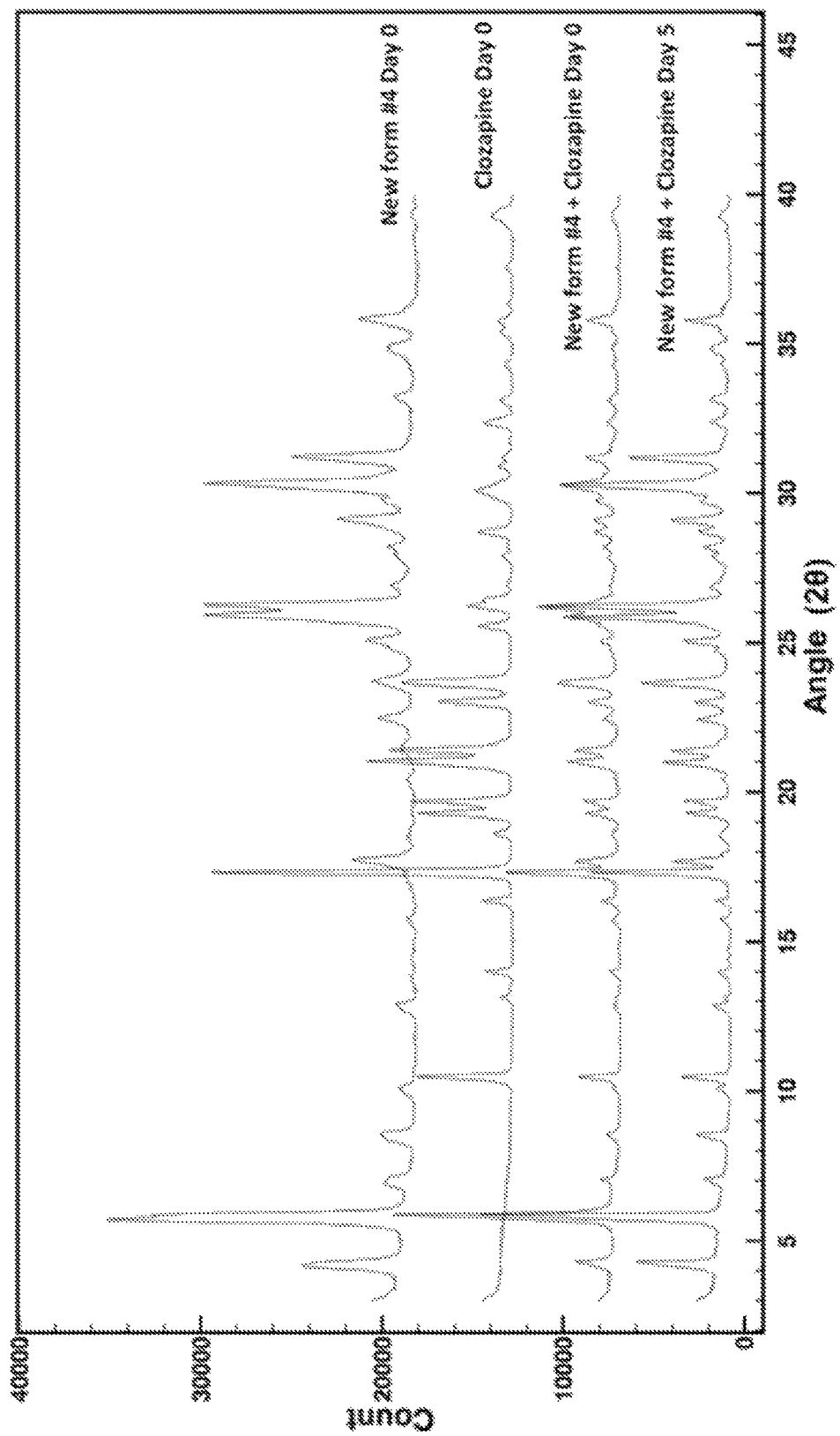
FIG. 15 shows no change of the X-ray powder diffraction (XRPD) of polymorphic form #4 of sodium benzoate combined with clozapine (300 mg) under high humidity conditions (of over 90% relative humidity) for 5 days.

In addition, the stability of the combination of sodium benzoate and clozapine was also examined under the high humidity condition. 500 mg of commercially available sodium benzoate from Merck and the polymorphic form #4 of sodium benzoate of the invention obtained from Example 4 was independently combined with 300 mg of clozapine, stored under high humidity condition (>90% RH), at room temperature for 5 days, and analyzed by XRPD. The XRPD results revealed that, after 5 days, there were significant changes in the XRPD pattern with peaks at a reflection angle 20 of approximately 6.2, 14.9, 15.9, 16.5, 20.5, 22.6, and 25.1 degrees and the appearance of a new peak at 22.9 degrees of sodium benzoate from Merck combined with clozapine. No change to the XRPD pattern of the polymorphic form #4 of sodium benzoate of the invention combined with clozapine was observed. The results are shown in FIGS. 14-15. It was thus illustrated that, when combined with a second therapeutic agent, the polymorphic form #4 of sodium benzoate of the invention was more stable than the tested commercial sodium benzoate products.

Figure 16:
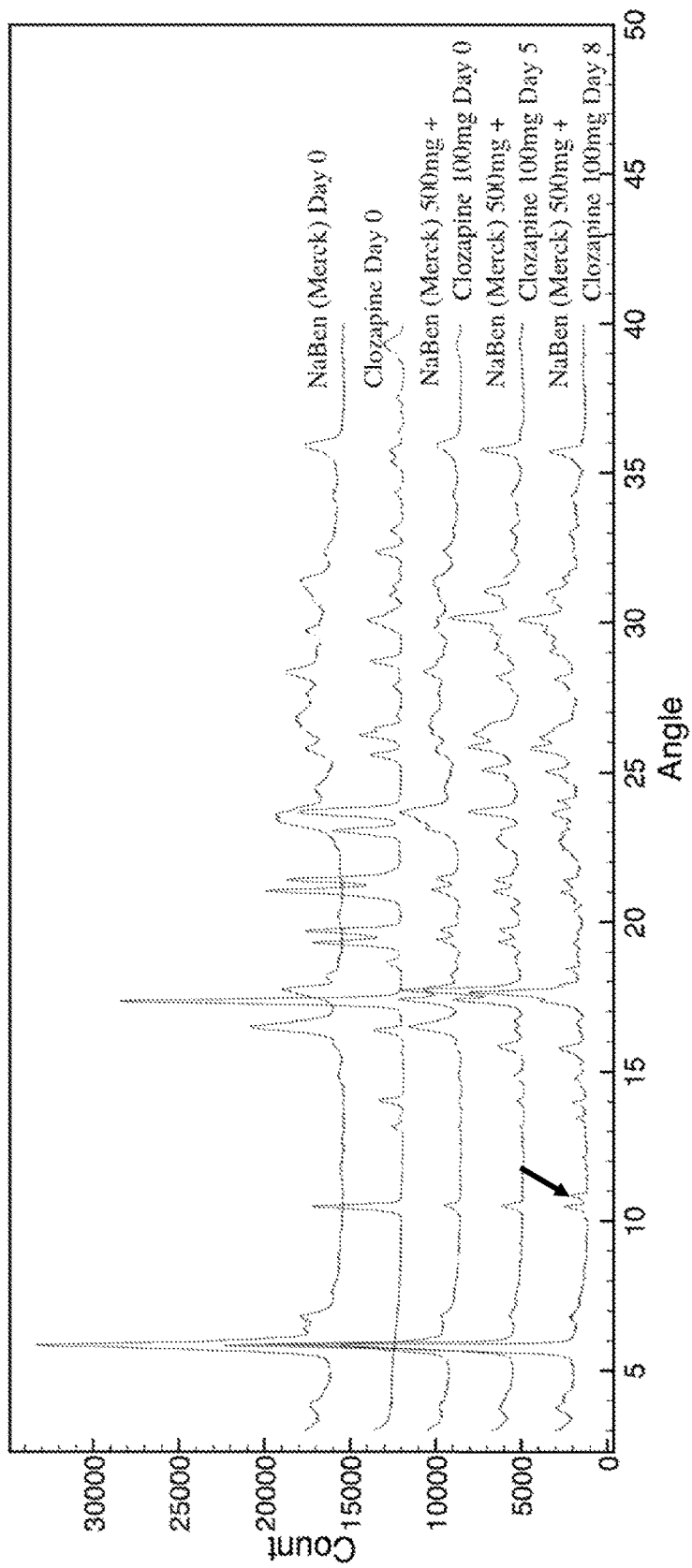
FIG. 16 shows the changes of X-ray powder diffraction (XRPD) of sodium benzoate (NaBen) from Merck combined with clozapine (100 mg) under high humidity conditions (>90% RH, room temperature) for 8 days.
Figure 17:
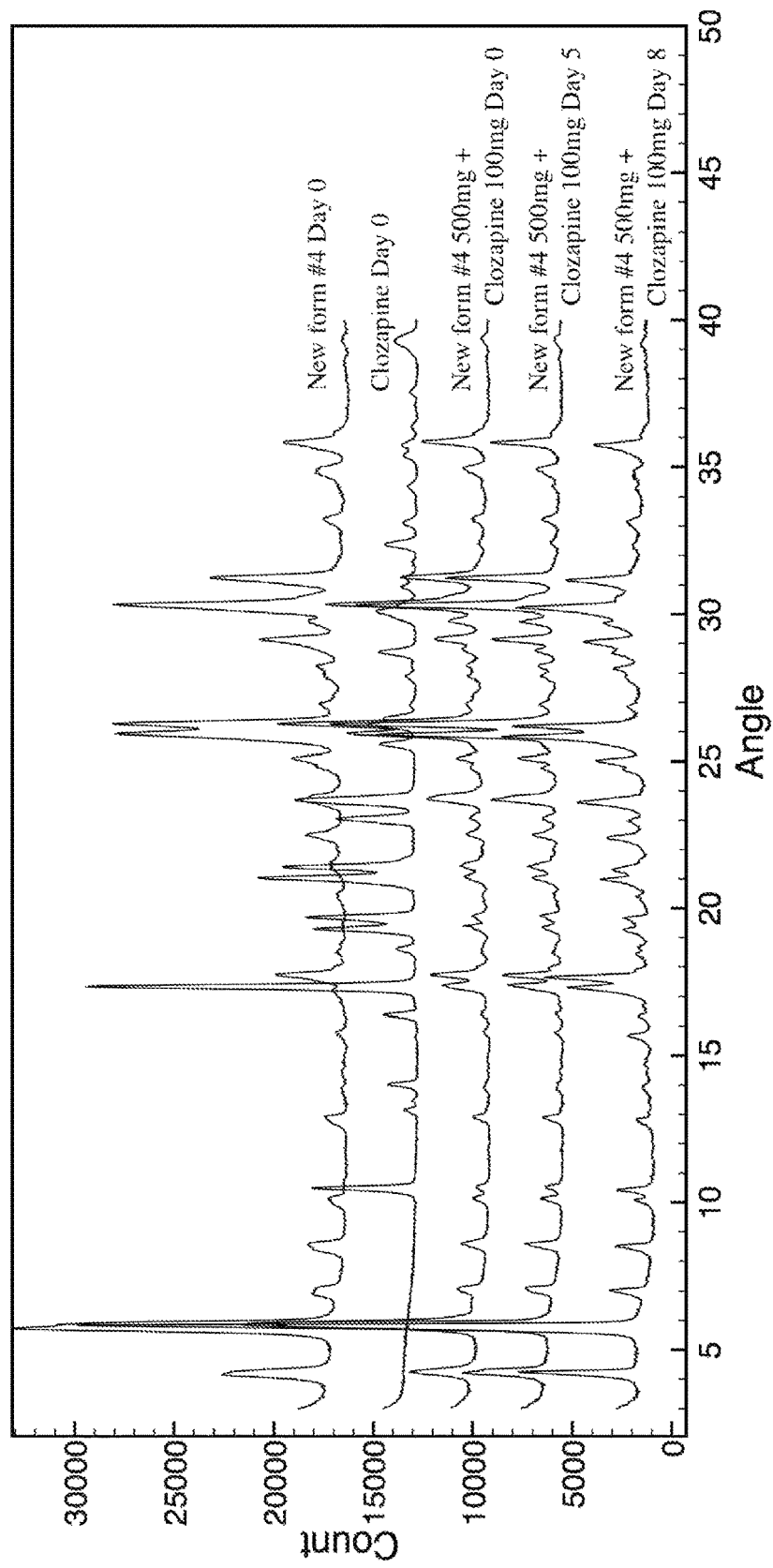
FIG. 17 shows no change of the X-ray powder diffraction (XRPD) of polymorphic form #4 of sodium benzoate combined with clozapine (100 mg) under high humidity conditions (>90% RH, room temperature) for 8 days.

Another stability test was held with 500 mg of commercially available sodium benzoate from Merck or the polymorphic form #4 of sodium benzoate of the invention independently combined with 100 mg of clozapine, stored under high humidity condition (>90% RH), at room temperature for 8 days. On day 8, the XRPD pattern of the combination of commercially available sodium benzoate and clozapine showed an additional new peak at 11°, as shown by an arrow in FIG. 16-17. However, the additional peak at 11° was not found in the XRPD pattern of the combination of the polymorphic form #4 of sodium benzoate of the invention and clozapine. In the following experiments, the appearance of the peak at 11° was deemed as deterioration of clozapine polymorph in the combination of clozapine and commercially available sodium benzoate.

2. Stability of Combination of Polymorphic Form #4 of Sodium Benzoate of the Invention and Clozapine, and Other Excipients Since humidity is a stability issue for the combination of sodium benzoate compound and clozapine, several excipients were chosen to test their influences on the stability under high humidity condition (>90% RH, room temperature). The results are shown in the Tables 1 and 2.

Comparing with boric acid, sodium alginate has a better effect in stabilizing the combination of sodium benzoate (purchased from Merck) and clozapine (see Table 1). In addition, the 11° peak, which indicates the deterioration of the combination of sodium benzoate (purchased from Merck) and clozapine, does not appear until day 30 when high dose of chitosan (60 mg) or sodium citrate (60 mg) further added in the composition (see Table 2).

TABLE 1

Stability test results under high humidity condition (>90% RH, room temperature) of sodium benzoate and clozapine mixed with different excipients

| Sample | 1 | 2 | 3 | 4 |
|---|---|---|---|---|
| Sodium benzoate (Merck) (mg) | 500 | 500 | 500 | 500 |
| Clozapine (mg) | 300 | 300 | 300 | 300 |
| Boric acid (mg) | 20 | 40 | — | — |
| Sodium alginate (mg) | — | — | 20 | 40 |
| TOTAL (mg) | 820 | 840 | 820 | 840 |
| Appearance of peak at 11° | Day 5 | Day 5 | Day 11 | Day 11 |

TABLE 2

Stability test results under high humidity condition (>90% RH, room temperature) of sodium benzoate and clozapine mixed with different excipients

| Sample | 5 | 6 | 7 | 8 | 9 | 10 | 11 | 12 | 13 | 14 |
|---|---|---|---|---|---|---|---|---|---|---|
| Sodium benzoate (Merck) (mg) | 500 | 500 | 500 | 500 | 500 | 500 | 500 | 500 | 500 | 500 |
| Clozapine (mg) | 300 | 300 | 300 | 300 | 300 | 300 | 300 | 300 | 300 | 300 |
| Sodium alginate (mg) | 40 | 40 | 40 | 40 | 40 | 40 | 40 | 40 | 40 | 40 |
| Chitosan (mg) | 30 | 60 | — | — | — | — | — | — | — | — |
| Sodium hyaluronate (mg) | — | — | 7.5 | 15 | — | — | — | — | — | — |
| Sodium stearyl fumarate (mg) | — | — | — | — | 7.5 | 15 | — | — | — | — |
| Sodium citrate (mg) | — | — | — | — | — | — | 30 | 60 | — | — |
| Sodium starch glycolate (mg) | — | — | — | — | — | — | — | — | 30 | 60 |
| TOTAL (mg) | 870 | 900 | 847.5 | 855 | 847.5 | 855 | 870 | 900 | 870 | 900 |
| Appearance of peak at 11° | Day 20 | Day 30 | Day 20 | Day 13 | Day 11 | Day 11 | Day 20 | Day 30 | Day 11 | Day 11 |

Example 9: Preparation of Tablets Comprising Sodium Benzoate Compound and Clozapine 1. Wet Granulation The active ingredients (e.g. any of the sodium benzoate compounds and clozapine) and excipients were milled and sieved by a 40-mesh screen separately. The milled and sieved powders were mixed in a mortar. 75% ethanol, which was used as a binder solution, was added slowly into the mortar to perform wet granulation. The obtained wet mass was screened by a 20-mesh screen for coarse screening. Then the moist granules were dried at 50° C. for 3 hours. The dried granules were further sieved twice: (1) by a 40-mesh screen, and the granules larger than 40-mesh were kept; and (2) by a 20-mesh screen, and the granules passed the screen were kept. After sieving with the 40- and 20-mesh screens, the granules having sizes between 20 and 40 meshes were obtained. The resulted granules were then blended with magnesium stearate as a lubricant for approximately 3 minutes, and the blend was compressed by ZP01 Single punch tablet press (Taizhou Liming Pharmaceutical Machinery Co., Ltd.) into tablets. The obtained tablets were weighted, and their hardness, friability, disintegration time and dissolution release time were tested.

2. Hardness Test

The obtained tablets were subjected to a hardness test, and the power (kg) needed for breaking the tested tablet was recorded. The harness of tablets was controlled between 5 to 10 kg.

3. Friability Test

Ten tablets were put in a tablet friability apparatus and rotated at 25±1 rpm for 100 circles. The test was determined as failed if any of the tested tablets were broken. When the tablets were not broken, they would be weighted to calculate their weight loss (%). The weight loss (%) should be lower than 1%.

4. Disintegration Test

Six tablets were put into water at 37±2° C. The test was determined as failed if these tablets were not disintegrated within 30 minutes. The disintegration time (minutes) of these tablets was recorded.

5. Dissolution Test

The dissolution test was performed based on the USP method for dissolution of clozapine. Six tablets were added into the dissolution medium (acetate buffer, pH 4.0) and subjected to the dissolution test. The volume of the dissolution medium was 500 mL and the rotation speed was of 100 rpm. The test was determined as failed if these tablets were not dissolved within 30 minutes. The dissolution time (minutes) of these tablets was recorded.

Both sodium alginate and sodium citrate enhance the immediate release effect, but the tablet formulations 1-2, which comprise sodium alginate and sodium citrate, flaked off during the dissolution test, and the addition of sodium starch glycolate (SSG) as a disintegrating agent improved this defect, as shown in Table 3.

TABLE 3

Tablet formulations

| Formulation | 1 | 2 | 3 |
|---|---|---|---|
| Sodium benzoate (Merck) (mg) | 500 | 500 | 500 |
| Clozapine (mg) | 300 | 200 | 300 |

TABLE 3-continued

Tablet formulations

| Formulation | 1 | 2 | 3 |
|---|---|---|---|
| Sodium alginate (mg) | 60 | 60 | 60 |
| Sodium citrate (mg) | 60 | 60 | 60 |
| Magnesium stearate (mg) | 10 | 10 | 10 |
| Sodium starch glycolate (mg) | — | — | 90 |
| TOTAL (mg) | 930 | 830 | 1020 |
| Hardness (kg) | 7~8 | 13-14 | 10 |
| Friability (%) | 0.73 | 0.51 | 0.6 |
| Disintegration time (min) | 20 | 19 | 13 |
| Dissolution release time (min) | <30 | <30 | 15 |

Tablet formulations comprising the combination of clozapine and commercially available sodium benzoate (purchased from Merck) or the polymorphic form #4 sodium benzoate obtained from Example 4, as shown in Tables 4 and 5, were then examined. The results showed that the tablets comprising the polymorphic form #4 of sodium benzoate of the invention had shorter disintegration time and dissolution release time, which were benefit for preparation of immediate release dosage form of drugs.

TABLE 4

Tablet formulations comprising commercially available sodium benzoate and clozapine

| Formulation | 4 | 5 | 6 | 7 | 8 | 9 | 10 | 11 |
|---|---|---|---|---|---|---|---|---|
| Sodium benzoate (Merck) (mg) | 500 | 500 | 500 | 500 | 500 | 500 | 500 | 500 |
| Clozapine (mg) | 300 | 300 | 300 | 300 | 200 | 200 | 200 | 200 |
| Sodium alginate (mg) | 50 | 70 | 50 | 70 | 50 | 70 | 50 | 70 |
| Sodium citrate (mg) | 50 | 70 | 60 | 60 | 50 | 70 | 60 | 60 |
| Magnesium stearate (mg) | 5 | 15 | 10 | 10 | 5 | 15 | 10 | 10 |
| Sodium starch glycolate (mg) | 80 | 100 | 100 | 80 | 80 | 100 | 100 | 80 |
| TOTAL (mg) | 985 | 1055 | 1020 | 1020 | 885 | 955 | 920 | 920 |
| Hardness (kg) | 9~10 | 9~10 | 9~10 | 9~10 | 10~11 | 10~11 | 10~11 | 10~11 |
| Friability (%) | 0.42 | 0.50 | 0.76 | 0.53 | 0.36 | 0.38 | 0.40 | 0.34 |
| Disintegration time (min) | 16~17 | 16~18 | 13~14 | 15~16 | 11~12 | 11~12 | 11~12 | 13~14 |
| Dissolution release time (min) | 14~15 | 15~16 | 13~14 | 15~16 | 11~12 | 12~13 | 11~12 | 13~14 |

TABLE 5

Tablet formulations comprising the polymorphic form #4 of sodium benzoate of the invention and clozapine

| Formulation | 12 | 13 | 14 | 15 | 16 | 17 | 18 | 19 |
|---|---|---|---|---|---|---|---|---|
| Polymorphic form #4 of sodium benzoate (mg) | 500 | 500 | 500 | 500 | 500 | 500 | 500 | 500 |
| Clozapine (mg) | 300 | 300 | 300 | 300 | 200 | 200 | 200 | 200 |
| Sodium alginate (mg) | 50 | 70 | 50 | 70 | 50 | 70 | 50 | 70 |
| Sodium citrate (mg) | 50 | 70 | 60 | 60 | 50 | 70 | 60 | 60 |
| Magnesium stearate (mg) | 5 | 15 | 10 | 10 | 5 | 15 | 10 | 10 |
| Sodium starch glycolate (mg) | 80 | 100 | 100 | 80 | 80 | 100 | 100 | 80 |
| TOTAL (mg) | 985 | 1055 | 1020 | 1020 | 885 | 955 | 920 | 920 |
| Hardness (kg) | 6~7 | 6~7 | 6~7 | 6~7 | 6~7 | 6~7 | 6~7 | 6~7 |
| Friability (%) | 0.68 | 0.71 | 0.67 | 0.63 | 0.52 | 0.69 | 0.66 | 0.78 |
| Disintegration time (min) | 5~6 | 6~7 | 5~6 | 6~7 | 5~6 | 6~7 | 5~6 | 5~6 |
| Dissolution release time (min) | 8~9 | 8~9 | 8~9 | 8~9 | 7~8 | 8~9 | 8~9 | 8~9 |

EQUIVALENTS AND SCOPE

In the claims, articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A pharmaceutical composition comprising 50 to 1000 mg of a sodium benzoate compound, 25 to 300 mg of clozapine, and a pharmaceutically acceptable excipient, wherein the pharmaceutical composition is in a solid dosage form, and wherein the sodium benzoate compound comprises a polymorphic form of sodium benzoate, which is characterized by an X-ray powder diffraction pattern comprising characteristic peaks at a reflection angle 2θ of about 5.9, 30.2, and 31.2 degrees.

2. The pharmaceutical composition of claim 1, wherein the polymorphic form of sodium benzoate is characterized by an X-ray powder diffraction pattern further comprising characteristic peaks at a reflection angle 2θ of about 4.3, 7.1, 8.6, 10.1, 10.7, 12.9, 13.8, 14.4, 17.2, 17.7, 18.5, 21.5, 22.0, 22.6, 23.7, 25.1, 25.9, 26.2, 26.9, 27.9, 28.2, 28.8, 29.1, 29.7, 33.2, 34.9, 35.8, 36.1, 39.3 degrees.

3. The pharmaceutical composition of claim 1, wherein the excipient is selected from the group consisting of boric acid, sodium alginate, sodium citrate, sodium hyaluronate, chitosan, magnesium stearate, sodium stearyl fumarate, colloidal silicon dioxide, talc, sodium starch glycolate, croscarmellose, crospovidone, and tannic acid.

4. The pharmaceutical composition of claim 1, which comprises 50 to 1000 mg of sodium benzoate, 25-300 mg of clozapine, 50-500 mg of sodium alginate, 50-400 mg of sodium citrate, 5-100 mg of magnesium stearate, and 80-200 mg of sodium starch glycolate.

5. The pharmaceutical composition of claim 1, wherein the solid dosage form is selected from the group consisting of tablet, dragee, capsule, pill, powder, and granule.

6. The pharmaceutical composition of claim 5, wherein the solid dosage form further comprises a film coating.

* * * * *